(12) United States Patent
Sanders et al.

(10) Patent No.: US 11,969,394 B2
(45) Date of Patent: Apr. 30, 2024

(54) SYRINGE ADAPTER

(71) Applicant: Becton Dickinson and Company Limited, Dun Laoghaire (IE)

(72) Inventors: Laurie Sanders, Glen Ridge, NJ (US); Jayeon Kim, River Edge, NJ (US); Antonio Righez Mesquita, Wayne, NJ (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 804 days.

(21) Appl. No.: 15/871,314

(22) Filed: Jan. 15, 2018

(65) Prior Publication Data

US 2018/0200146 A1 Jul. 19, 2018

Related U.S. Application Data

(60) Provisional application No. 62/447,032, filed on Jan. 17, 2017.

(51) Int. Cl.
*A61J 1/20* (2006.01)
*A61J 1/14* (2023.01)
(Continued)

(52) U.S. Cl.
CPC ........... *A61J 1/2096* (2013.01); *A61J 1/1406* (2013.01); *A61J 1/1443* (2013.01); *A61J 1/201* (2015.05);
(Continued)

(58) Field of Classification Search
CPC ........ A61J 1/2096; A61J 1/201; A61J 1/2055; A61J 1/1406; A61J 1/1443; A61J 1/2048;
(Continued)

(56) References Cited

U.S. PATENT DOCUMENTS

| 4,436,125 A | 3/1984 | Blenkush |
| 4,564,054 A | 1/1986 | Gustavsson |

(Continued)

FOREIGN PATENT DOCUMENTS

| CN | 1767799 A | 5/2006 |
| CN | 102470074 A | 5/2012 |

(Continued)

OTHER PUBLICATIONS

Definition of Annular (Year: 2020).*
(Continued)

*Primary Examiner* — Benjamin J Klein
*Assistant Examiner* — Gabriella E Burnette
(74) *Attorney, Agent, or Firm* — The Webb Law Firm

(57) ABSTRACT

A syringe adapter is provided. The adapter includes a housing having a first end and a second end positioned opposite the first end. The housing may include a first portion and a second portion connected to the first portion. The first end of the housing can include a connector configured to be secured to a syringe barrel. The adapter also includes a cannula positioned within the housing and a seal arrangement including a membrane positioned within the housing and movable within the housing. The first portion of the housing can be connected to the second portion via axial and radial interference between the first portion and the second portion of the housing.

18 Claims, 17 Drawing Sheets

(51) Int. Cl.
*A61M 5/32* (2006.01)
*A61M 39/10* (2006.01)
*A61M 39/22* (2006.01)

(52) U.S. Cl.
CPC .......... *A61J 1/2055* (2015.05); *A61M 5/3202* (2013.01); *A61M 39/10* (2013.01); *A61M 39/221* (2013.01)

(58) Field of Classification Search
CPC ...... A61J 1/20; A61M 5/3203; A61M 5/1782; A61M 39/221; A61M 39/10
See application file for complete search history.

(56) References Cited

U.S. PATENT DOCUMENTS

| | | | |
|---|---|---|---|
| 4,576,211 A | | 3/1986 | Valentini et al. |
| 4,986,322 A | * | 1/1991 | Chibret .............. B65D 81/3211 141/366 |
| 5,104,158 A | | 4/1992 | Meyer et al. |
| 5,122,123 A | | 6/1992 | Vaillancourt |
| 5,492,147 A | | 2/1996 | Challender et al. |
| 5,810,792 A | | 9/1998 | Fangrow, Jr. et al. |
| 7,648,491 B2 | | 1/2010 | Rogers |
| 7,975,733 B2 | | 7/2011 | Horppu et al. |
| 8,122,923 B2 | | 2/2012 | Kraus et al. |
| 8,196,614 B2 | | 6/2012 | Kriheli |
| 8,267,127 B2 | | 9/2012 | Kriheli |
| D708,518 S | | 7/2014 | Ivosevic |
| 8,790,327 B2 | | 7/2014 | Takemoto |
| D710,196 S | | 8/2014 | Ivosevic |
| 8,900,212 B2 | | 12/2014 | Kubo |
| 9,126,029 B2 | | 9/2015 | Fangrow et al. |
| 9,168,366 B2 | | 10/2015 | Fangrow et al. |
| 9,381,135 B2 | | 7/2016 | Reynolds et al. |
| 9,381,137 B2 | | 7/2016 | Garfield et al. |
| 9,414,990 B2 | | 8/2016 | Ivosevic et al. |
| 9,414,991 B2 | | 8/2016 | Sanders et al. |
| 9,510,997 B2 | | 12/2016 | Kriheli et al. |
| 9,597,260 B2 | | 3/2017 | Vosevic et al. |
| 9,610,222 B2 | | 4/2017 | Kriheli et al. |
| 9,636,278 B2 | | 5/2017 | Sanders et al. |
| 9,642,775 B2 | | 5/2017 | Sanders et al. |
| 9,724,269 B2 | | 8/2017 | Sjogren et al. |
| 9,750,926 B2 | | 9/2017 | Lopez et al. |
| 9,833,605 B2 | | 12/2017 | Sanders et al. |
| 9,855,192 B2 | | 1/2018 | Kim et al. |
| 2005/0107739 A1 | * | 5/2005 | Palma ................ A61M 39/1011 604/104 |
| 2008/0009783 A1 | | 1/2008 | Branderburger et al. |
| 2009/0069783 A1 | | 3/2009 | Ellstrom et al. |
| 2013/0006211 A1 | | 1/2013 | Takemoto |
| 2013/0076019 A1 | | 3/2013 | Takemoto |
| 2014/0074038 A1 | | 3/2014 | Ivosevic |
| 2014/0150925 A1 | | 6/2014 | Sjogren et al. |
| 2014/0246616 A1 | * | 9/2014 | Fangrow ................ F16L 29/00 251/148 |
| 2014/0261877 A1 | | 9/2014 | Ivosevic et al. |
| 2014/0276649 A1 | | 9/2014 | Ivosevic et al. |
| 2014/0303601 A1 | * | 10/2014 | Fangrow ............... A61M 39/10 604/537 |
| 2015/0216764 A1 | * | 8/2015 | Carrel ................. B65D 51/002 604/403 |
| 2015/0297454 A1 | * | 10/2015 | Sanders ................ A61J 1/2055 604/414 |
| 2015/0297456 A1 | | 10/2015 | Marici et al. |
| 2015/0297459 A1 | | 10/2015 | Sanders |
| 2015/0297839 A1 | | 10/2015 | Sanders et al. |
| 2015/0297881 A1 | * | 10/2015 | Sanders ................ A61J 1/1406 604/535 |
| 2016/0136412 A1 | | 5/2016 | Mckinnon et al. |
| 2016/0271017 A1 | | 9/2016 | Weir et al. |
| 2016/0331637 A1 | | 11/2016 | Sanders et al. |
| 2016/0361504 A1 | | 12/2016 | Kim et al. |
| 2017/0258682 A1 | | 9/2017 | Kriheli |
| 2018/0028402 A1 | | 2/2018 | Kriheli et al. |
| 2018/0071506 A1 | | 3/2018 | Sanders et al. |
| 2018/0085286 A1 | | 3/2018 | Kim et al. |
| 2020/0155770 A1 | | 5/2020 | Kim et al. |

FOREIGN PATENT DOCUMENTS

| | | |
|---|---|---|
| CN | 103167857 A1 | 6/2013 |
| CN | 103501751 A | 1/2014 |
| CN | 111450407 A | 7/2020 |
| IN | 206026788 U | 3/2017 |
| WO | 2012117648 A1 | 9/2012 |

OTHER PUBLICATIONS

Definition of triangular (Year: 2020).*
Definition of "into" Merriam Webster Dictionary https://www.merriam-webster.com/dictionary/into (Year: 2023).*

* cited by examiner

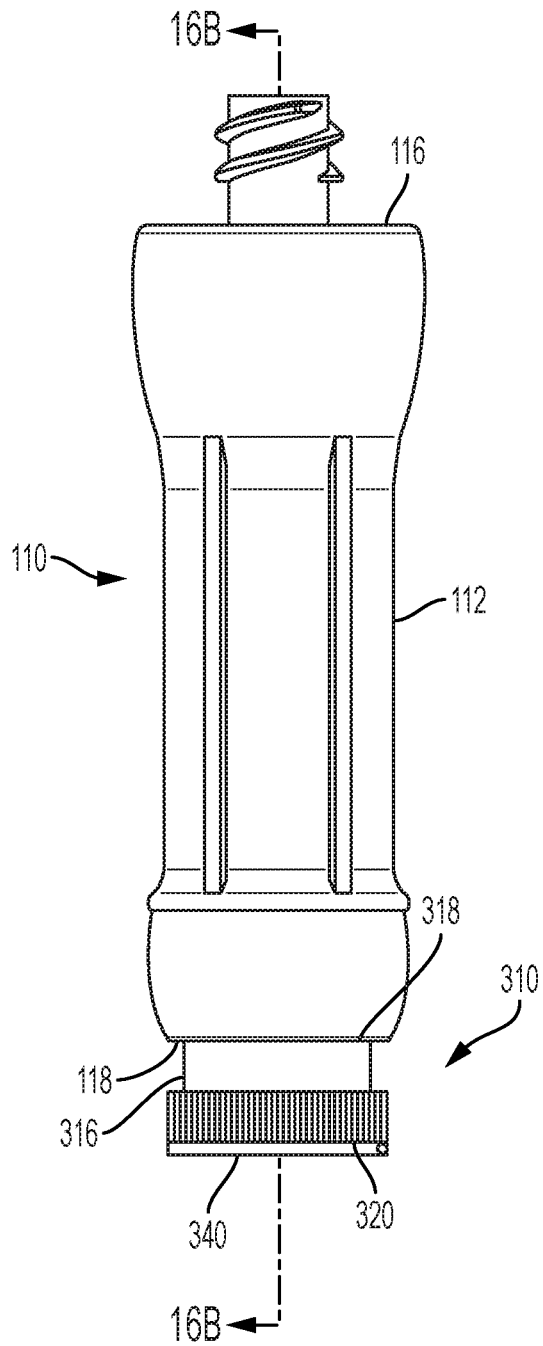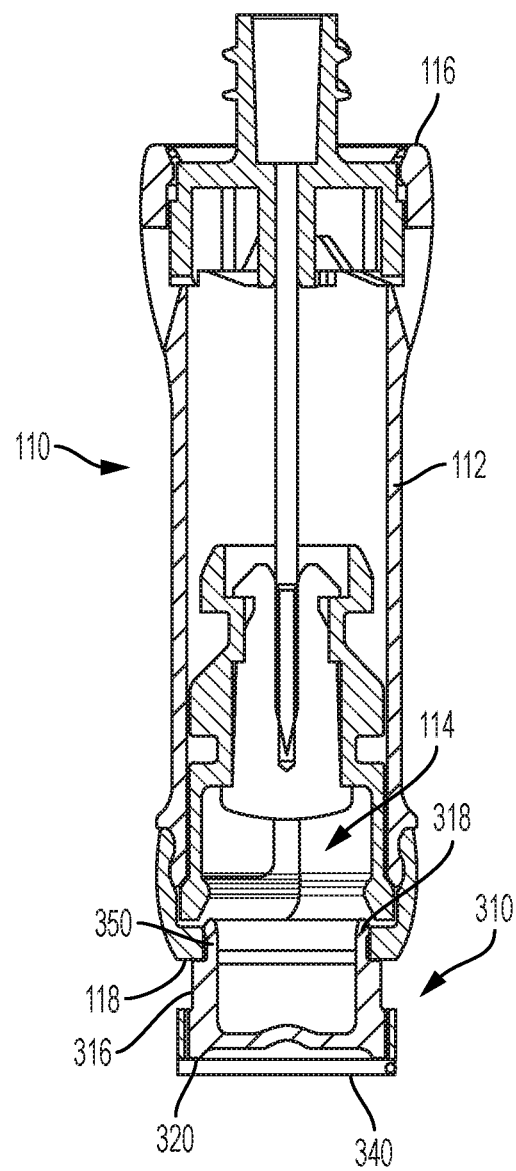
FIG. 16A
FIG. 16B

SYRINGE ADAPTER

CROSS-REFERENCE TO RELATED APPLICATION

This application claims priority to U.S. Provisional Application Ser. No. 62/447,032, filed Jan. 17, 2017, which is hereby incorporated by reference in its entirety.

BACKGROUND OF THE INVENTION

Field of the Invention

The present invention relates to a syringe adapter for connecting a syringe to another medical device or fluid container and, more particularly, to a syringe adapter including a housing formed from two connected portions or pieces.

Description of Related Art

Healthcare clinicians, such as pharmacists and nurses, can be subject to acute and long term health risks as a result of repeated exposure to drugs or solvents, which may escape into the air during drug preparation, drug administration, and other similar handling activities. For example, when performing infusions, it is often necessary to inject a drug or other medical substance into an infusion fluid inside an infusion bag or other infusion fluid container. This injection is often performed by penetrating a septum or other fluid barrier of an injection port on the infusion bag or on the infusion fluid line with a needle of a syringe filled with the medical fluid in question. Before penetrating the septum, it may also be necessary to transfer the medical fluid from a vial to a syringe and then from the syringe to the container. In each of these steps, the clinician or care provider may be exposed to the medical fluid resulting in contamination from, for example, vaporized medical fluids or from contaminants released as an aerosol. For example, contamination may occur by breathing the vaporized or aerosol contaminates into the lungs. Contamination may also occur when vaporized or aerosol contaminants condense on and then penetrate the clinician's or care provider's skin. In some instances, such condensed contaminates may even penetrate protective gloves.

Unfortunately, exposure to contaminants may, on a long term basis, give rise to unacceptably high concentrations of medicament or contaminants in the clinician or care provider's blood or body tissue. Risk of contamination is increased due to the many transferring steps between containers which must occur during preparation of complex infusions. For these reasons, closed system transfer devices (CSTDs) have been developed to ensure that the medicament is contained in the transfer device during transfer of the medicament. A CSTD generally includes a syringe adapter for connection to a syringe and another adapter (often referred to as a patient connector) for connection to a vial, a second syringe, a fluid container, or a conduit providing fluid access to the patient's circulatory system. In use, the clinician or care provider may reconstitute a powdered or lyophilized compound with saline or some other reconstitution medium by attaching the syringe to the vial via connection of the respective adapters. The drug is then reconstituted by injecting fluid from the syringe, through the respective adapters, and into the vial. In some instances, the reconstituted infusion may then be aspirated into the syringe. After aspiration, the adapters can be disconnected from one another. The clinician or care provider may then attach the syringe to another adapter to transfer fluid from the syringe to a fluid conduit or patient delivery device, such as an IV line or syringe, for administration to the patient. In one or more of these connecting steps, the clinician may need to disinfect portions of the adapter(s) to ensure a safe connection therebetween.

In view of the multiple connections that must be performed during reconstitution of a drug or therapeutic agent, devices and assemblies which assist clinicians in preparing adapters for connection with one another and/or with a patient line are needed. The syringe adapter, cap, and assembly disclosed herein are configured to address these issues.

SUMMARY OF THE INVENTION

According to one aspect of the disclosure, a syringe adapter is provided. The syringe adapter includes a housing having a first end and a second end positioned opposite the first end. The housing includes a first portion and a second portion connected to the first portion. The first end of the housing includes a connector configured to be secured to a syringe barrel. The adapter also includes a cannula positioned within the housing and a seal arrangement including a membrane positioned within the housing and movable within the housing. The first portion of the housing can be connected to the second portion via axial and radial interference between the first portion and the second portion of the housing.

In some examples, the second portion of the housing can include an annular triangular interface. The annular triangular interface of the second portion of the housing can engage the first portion of the housing to provide the axial interference between the first portion of the housing and the second portion of the housing. The annular triangular interface of the second portion of the housing can engage a planar interface of the first portion of the housing. For example, the planar interface of the first portion of the housing can extend about perpendicularly to a longitudinal axis of the housing. Optionally, the annular triangular interface of the second portion of the housing can include a pointed end configured to engage the first portion of the housing. The annular triangular interface of the second portion of the housing can also include a radially inwardly sloped surface extending from the pointed end of the annular triangular interface. The first portion of the housing can include a plurality of projections, which can be configured to engage the second portion of the housing to provide the radial interference between the first portion of the housing and the second portion of the housing.

In some examples, the first portion of the housing can include a plurality of projections. The plurality of projections of the first portion of the housing can engage the second portion of the housing to provide the radial interference between the first portion of the housing and the second portion of the housing. The plurality of projections can be spaced apart around a circumference of the first portion of the housing. For example, the plurality of projections can each extend radially outward from the first portion of the housing. Optionally, the plurality of projections are configured to press into the first portion of the housing, when the first portion of the housing is connected to the second portion of the housing.

In some examples, the second portion of the housing can include a plurality of teeth, which engage the first portion of the housing to provide the axial interference between the first portion of the housing and the second portion of the housing. Each of the plurality of teeth can extend in an axial direction. Optionally, each of the plurality of teeth are configured to press into the first portion of the housing, when the second portion of the housing is connected to the first portion of the housing.

In some examples, the plurality of teeth can each provide uneven distribution of stress between the first portion of the housing and the second portion of the housing, when the second portion of the housing is connected to the first portion of the housing. For example, the plurality of teeth can be disposed about and extend from an annular first end of the second portion. The plurality of teeth can be spaced apart and separated by a substantially planar surface. The plurality of teeth can be connected together about the annular first end of the second portion of the housing.

In some examples, the connector is rotatably mounted to the first portion of the housing. The cannula can be secured to the connector and at least partially enclosed within the housing.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

FIG. 16A is a front view of a syringe adapter mounted to another embodiment of a protective cap according to an aspect of the disclosure;

FIG. 16B is a cross-sectional view of the syringe adapter and cap of FIG. 16A taken along line 16B-16B;

DESCRIPTION OF THE INVENTION

Figure 1:
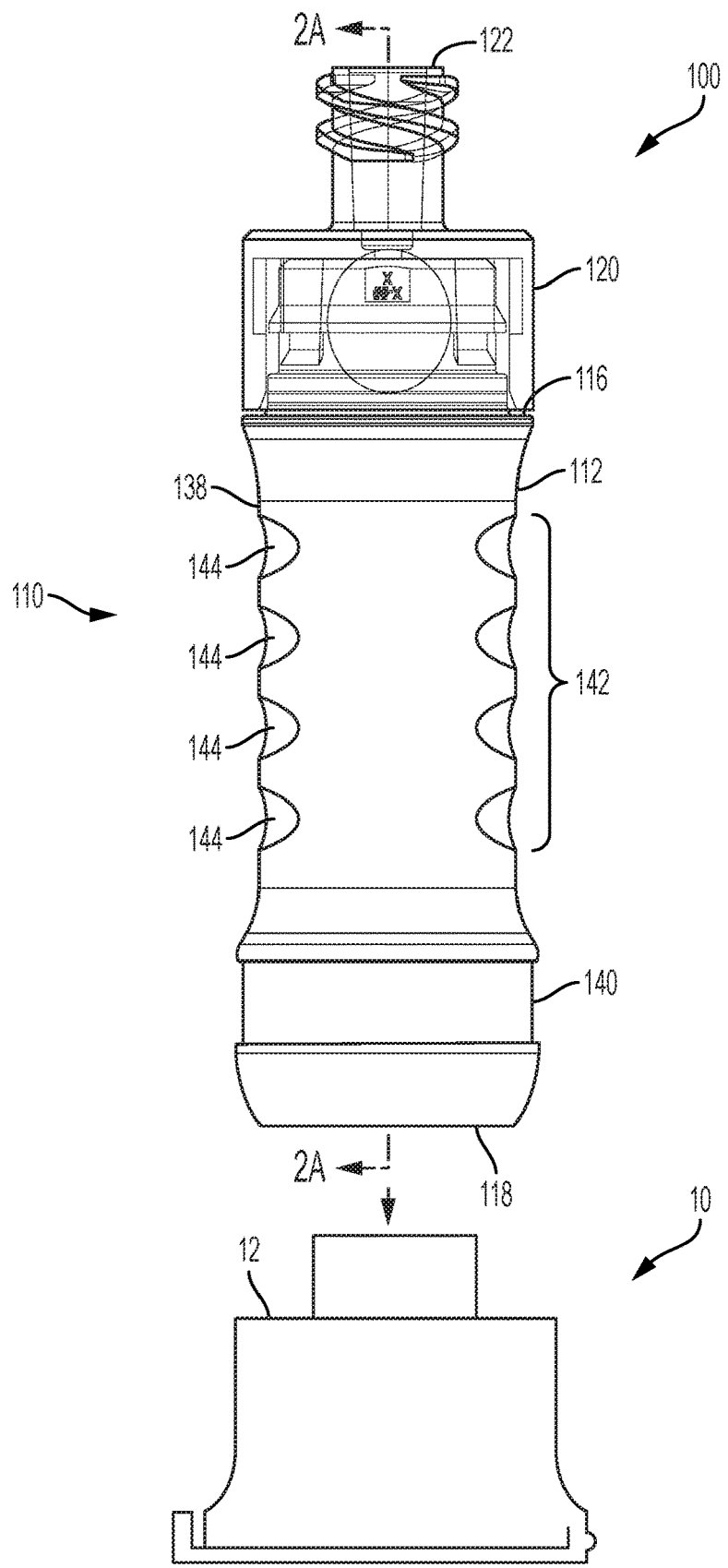
FIG. 1 is a front view of an assembly including a syringe adapter and cap according to an aspect of the present disclosure.

The illustrations generally show preferred and non-limiting aspects of the systems and methods of the present disclosure. While the descriptions present various aspects of the devices, it should not be interpreted in any way as limiting the disclosure. Furthermore, modifications, concepts, and applications of the disclosure's aspects are to be interpreted by those skilled in the art as being encompassed by, but not limited to, the illustrations and descriptions herein.

Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the drawing figures. The term "proximal" refers to the direction toward the center or central region of the device. The term "distal" refers to the outward direction extending away from the central region of the device. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structures, construction and method of operation, and many advantages may be understood and appreciated.

According to an aspect of the disclosure, a syringe adapter for connecting a syringe to another medical device or fluid container is provided. The medical device can be, for example, a patient line, vial adapter, fluid container, or injector. In other examples, the container can be a medical vial, syringe barrel, IV bag, or similar container for holding a fluid to be administered to a patient. The syringe adapter can be used to facilitate closed transfer of fluids between the syringe and medical device or fluid container. The syringe adapter can include a housing formed from a first portion, such as a first grip portion, inserted into a second portion, such as a second grip portion. The first portion can be connected to the second portion by an axial interference and/or a radial interference. Axial interference can refer to engagements between structures of the first portion of the housing and the second portion of the housing which prevent or inhibit either pulling the respective portions of the housing away from one another (e.g., disconnecting the portions of the housing) and/or pushing the first portion of the housing farther into the second portion of the housing. For example, axial interference can refer to situations where the first portion is essentially locked to the second portion to prevent axial movement of the first portion relative to the second portion. In a similar manner, radial interference can refer to structures that prevent or inhibit twisting of the portions of the housing relative to one another. A syringe adapter including both axial and radial interference structures, in combination, helps to more securely lock the portions of the housing in place.

According to another aspect of the disclosure, a protective cap for a syringe adapter is provided. An exemplary syringe adapter that can be used with the protective cap is described in United States Patent Appl. Pub. No. 2015/0297454, which is incorporated by reference herein in its entirety. The cap is configured to allow a user to disinfect an interior of the syringe adapter without removing the cap therefrom. For example, the cap can be configured to allow a user to insert a swab (e.g., a cotton swab immersed in a disinfecting agent, such as isopropyl alcohol) to disinfect an interior of the adapter without removing the cap from the adapter. In some examples, the cap can include a cover including a door or window configured to be opened by the user to allow the user to access the interior of the syringe adapter. In other examples, the cap can include a disinfecting swab or pad mounted thereto. The swab or pad can be positioned to be inserted into the interior of the syringe adapter when the cap is removably mounted to the adapter.

Figure 2A:
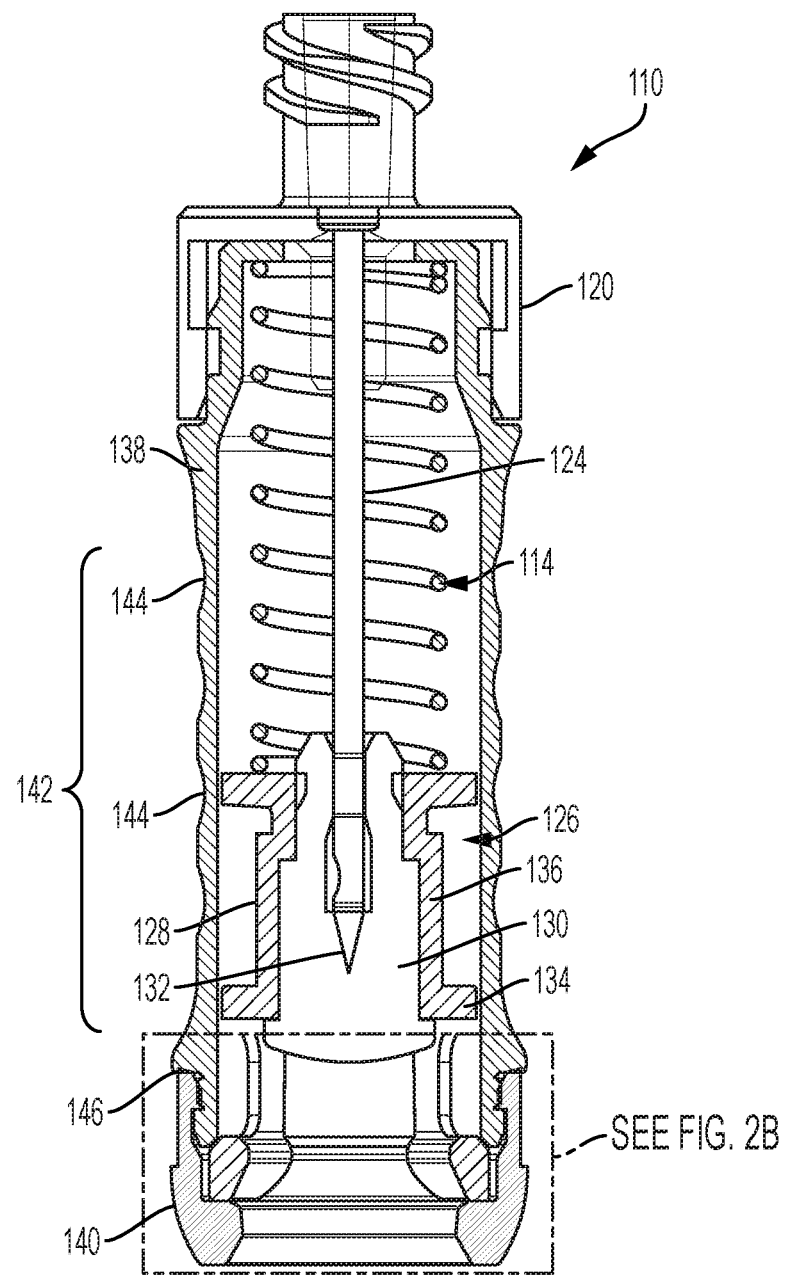
FIG. 2A is a cross-sectional view of the syringe adapter of FIG. 1 taken along line 2A-2A.
Figure 2B:
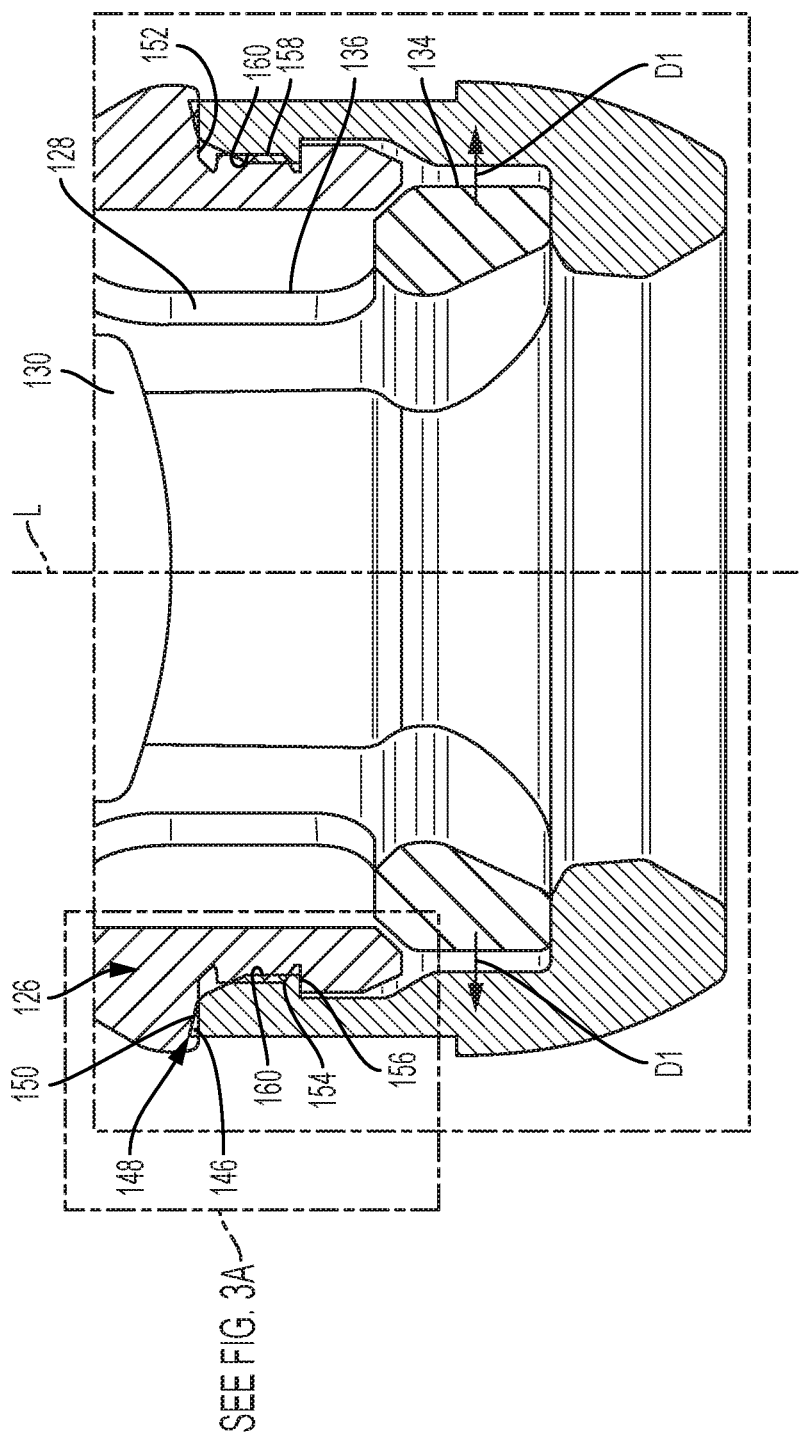
FIG. 2B is an enlarged cross-sectional view of the portion of the syringe adapter of FIG. 2A enclosed by shape 2B.

With reference to FIG. 1, an exemplary syringe adapter assembly 100 for establishing fluid communication between a syringe (not shown) and a connector (referred to hereinafter as "a patient connector") mounted to a patient line or container is illustrated. The assembly 100 may also be utilized in connection with other components of a fluid transfer system and/or a closed system transfer device including, but not limited to, a vial adapter, an IV bag spike, and an IV line. The assembly 100 can include a syringe adapter 110 and a protective cap 10. The syringe adapter 110 generally includes a housing 112 defining an interior 114 (shown in FIGS. 2A and 2B). The housing 112 includes a first or proximal end 116 configured to be directly or indirectly mounted to the syringe and an open second or distal end 118. The syringe adapter 110 can include a syringe connector 120 disposed at the proximal end 116 thereof and configured to engage the syringe. For example, the syringe connector 120 can include a syringe port 122, such as a luer connector or threaded connector, configured to engage a corresponding structure of the syringe.

In some examples, the syringe adapter 110 is configured to be removably mounted to a protective cap 10 by, for example, pressing the open distal end 118 of the adapter housing 112 into an open proximal end 12 of the cap 10. For example, the housing 112 can be snap-fit into the cap 10. As discussed herein, the cap 10 can include various locking and/or attachment structures for maintaining the connection between the adapter 110 and the cap 10. In some examples, the cap 10 can be configured to partially enclose the open distal end 118 of the housing, for example, to prevent contamination of the adapter housing 112. In some examples, the cap 10 can be transitioned to an open position to allow a user to access the interior 114 of the syringe adapter 110 without removing the cap 10 therefrom.

Exemplary Syringe Adapter

FIGS. 1-6 show aspects of an exemplary syringe adapter 110 which can be used with the protective cap 10. As shown in FIG. 2A, the syringe adapter 110 can include a needle cannula 124 mounted to and extending distally from the connector 120 into the interior 114 of the housing 112. As shown in FIGS. 2A and 2B, the adapter 110 also includes a seal arrangement, generally denoted by 126, including a socket or collet 128 slidably mounted into the interior 114 of the housing 112. The collet 128 is movable through the interior 114 of the housing 112 between a distal or pre-use position (shown in FIGS. 2A and 2B) and a proximal or in-use position. The seal arrangement 126 also includes a piercable membrane or septum 130 mounted to the collet 128. When the collet 128 is in its distal or pre-use position, a distal tip 132 (shown in FIG. 2A) of the cannula 124 is entirely enclosed by the septum 130 for preventing contamination prior to use. The collet 128 includes a distal flange 134 and legs 136 configured to grasp a portion of the patient connector (not shown) or another adapter to mount the syringe adapter 110 thereto. In some examples, the flange 134 and/or collet legs 136 can be radially inwardly biased to grasp the patient connector. When the patient connector is inserted in the open distal end 118 of the adapter 110, the flange 134 and/or legs 136 are pushed radially outward to a grip or recessed position in the direction identified by arrows D1 in FIG. 2B.

In use, once the patient connector is mounted to the distal end 118 of the adapter 110, the adapter 110 is activated by moving the collet 128 from the distal or pre-use position (shown in FIGS. 2A and 2B) to the proximal or use position. Moving the collet 128 in the proximal direction causes the distal tip 132 of the needle cannula 124 to pierce the septum or seal 130 thereby bringing the needle cannula 124 into contact with the patient connector or another adapter. Continued proximal movement of the collet 128 can bring the needle cannula 124 into fluid connection with another container or medical device mounted to the patient connector or adapter, thereby establishing fluid communication between the syringe and the container or medical device through the syringe adapter 110.

With reference again to FIGS. 1-6, the adapter housing 112 can be formed from two or more portions mounted together to enclose the interior 114. For example, the housing 112 can include a first portion 138 inserted into and/or connected to a second portion 140. In some examples, the first portion 138 of the housing 112 can include a grip arrangement 142 (shown in FIGS. 1 and 2A), which is shown as two pairs of elliptical recesses 144 (shown in FIGS. 1 and 2A). Other suitable grip arrangements may also be utilized for facilitating holding and/or manipulating the adapter 110.

In some examples, the first portion 138 of the housing 112 can be connected to the second portion 140 via axial and radial interference between the first portion 138 and the second portion 140 to effectively lock the portions 138, 140 together. With specific reference to FIGS. 2B, 3A, 3B, 5A, and 5B, in some examples, the second portion 140 includes an annular triangular interface, generally shown as 146, which engages the first portion 138 to form the axial interference. The annular triangular interface 146 can include a pointed end 148 and a radially inwardly directed sloped annular top surface 150 extending therefrom. The annular triangular interface 146 is configured to press into the first portion 138 of the housing 112 to lock the portions 138, 140 together. In some instances, the annular triangular interface 146 is positioned to press into a corresponding annular planar interface or surface 152, such as an annular planar wall, (shown in FIGS. 2B, 3A, and 3B) of the first portion 138. The planar interface or surface 152, such as the annular planar wall, can extend about perpendicularly to a longitudinal axis L of the housing 112. For example, the annular planar interface or surface 152, such as the annular planar wall, can be an annular horizontal wall that extends about perpendicularly to the longitudinal axis L of the housing 112, as shown in FIG. 4A. The annular triangular interference 146 can press or bite into the annular planar interface or surface 152 to form a suitable connection therewith.

Figure 3A:
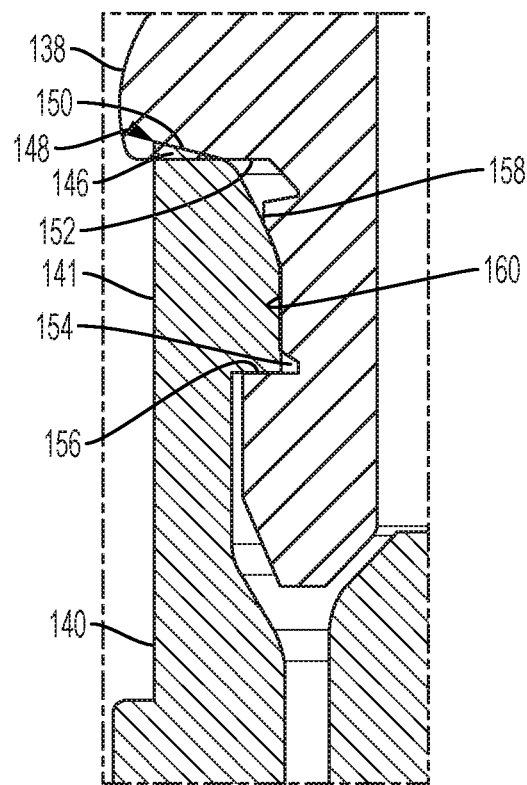
FIG. 3A is an enlarged cross-sectional view of a portion of the syringe adapter of FIG. 2A enclosed by shape 3A.
Figure 3B:
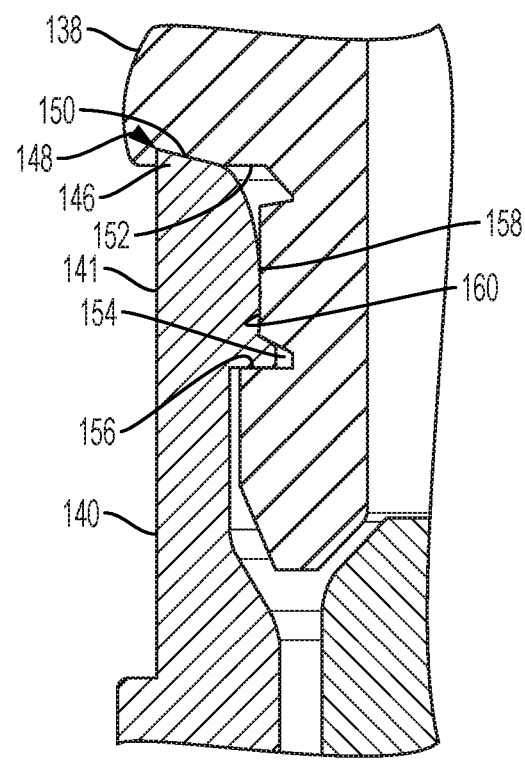
FIG. 3B is a cross-sectional view of another portion of the syringe adapter of FIG. 2A.
Figure 4A:
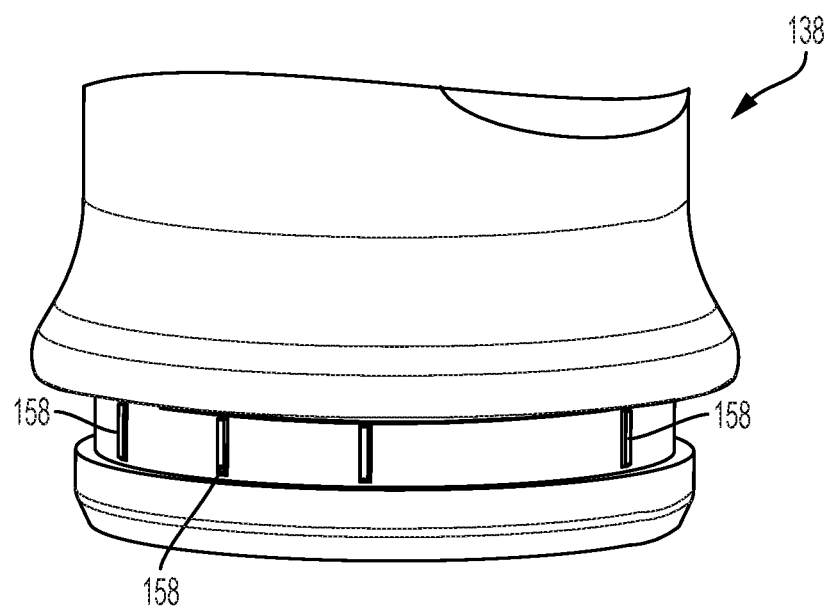
FIG. 4A is a front view of a first portion of a housing of the syringe adapter of FIG. 1.

In one example, an engagement between opposing bulbous portions or protrusions extending distally from the first portion 138 and proximally from the second portion 140 may also contribute to the axial interference, as shown in FIGS. 3A and 3B. For example, the second portion 140 of the housing 112 can include a bulbous portion or protrusion 154 configured to engage a corresponding shelf or ledge 156 of the first portion 138. The protrusion 154 of the second portion 140 can be a radially inwardly extending structure positioned at a proximal end 141 of the second portion 140. In some examples, the protrusion 154 can be radially inwardly biased against the ledge 156 to lock the first portion 138 of the housing 112 to the second portion 140. Contact between the protrusion 154 and ledge 156 prevents or make it more difficult for a user to pull the first portion 138 away from and/or out of the second portion 140.

Figure 4B:
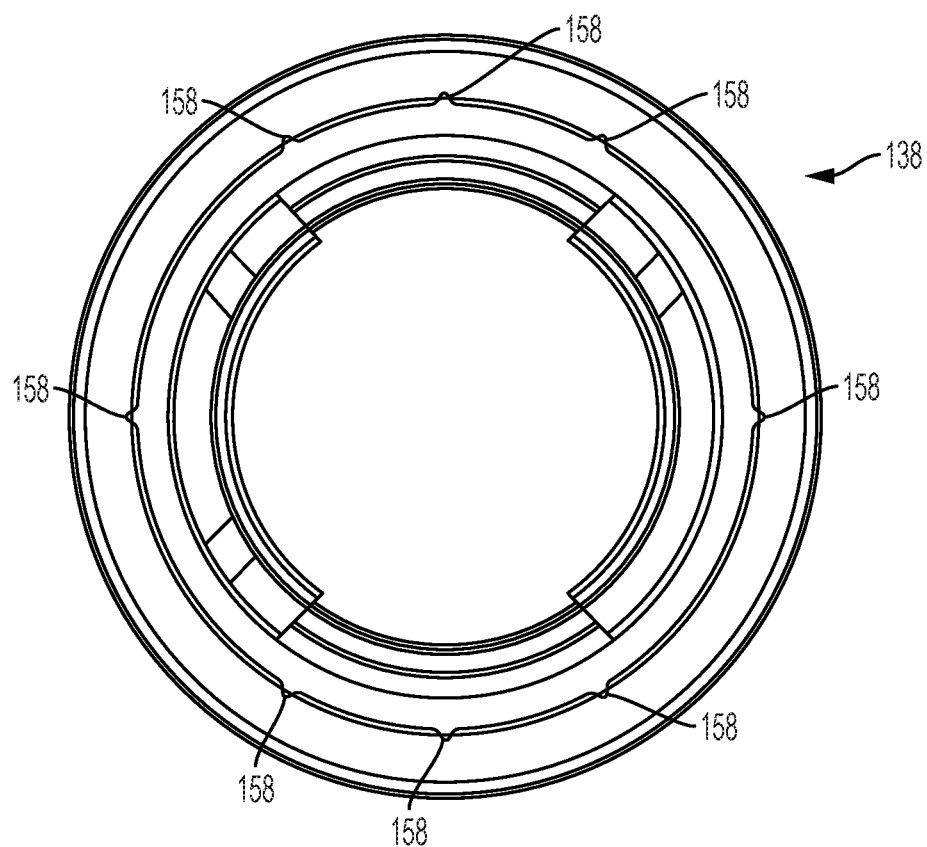
FIG. 4B is a bottom view of the first portion of the syringe adapter housing of FIG. 4A.
Figure 5A:
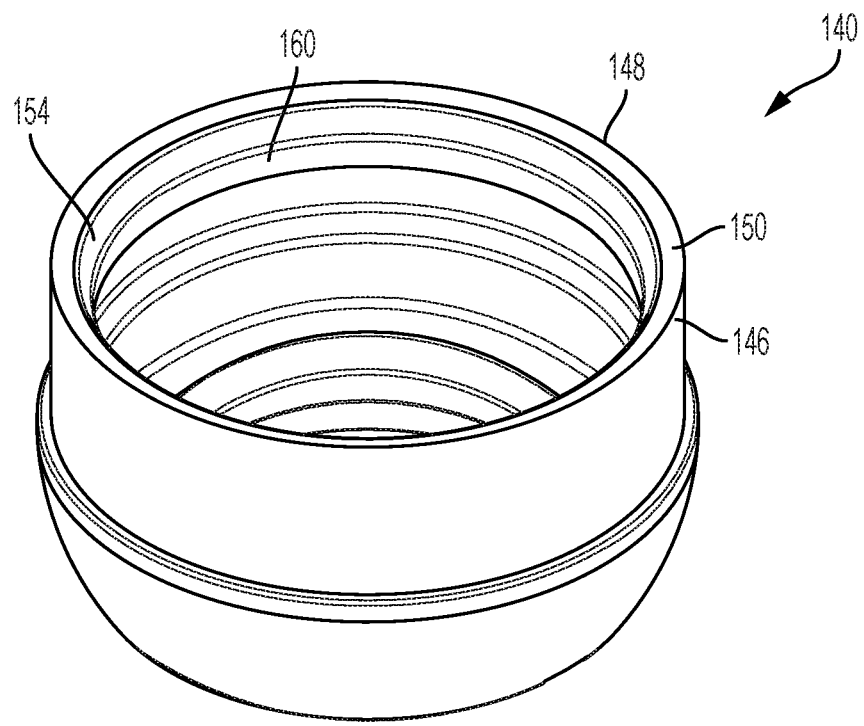
FIG. 5A is a perspective view of a second portion of the housing of the syringe adapter of FIG. 1.
Figure 5B:
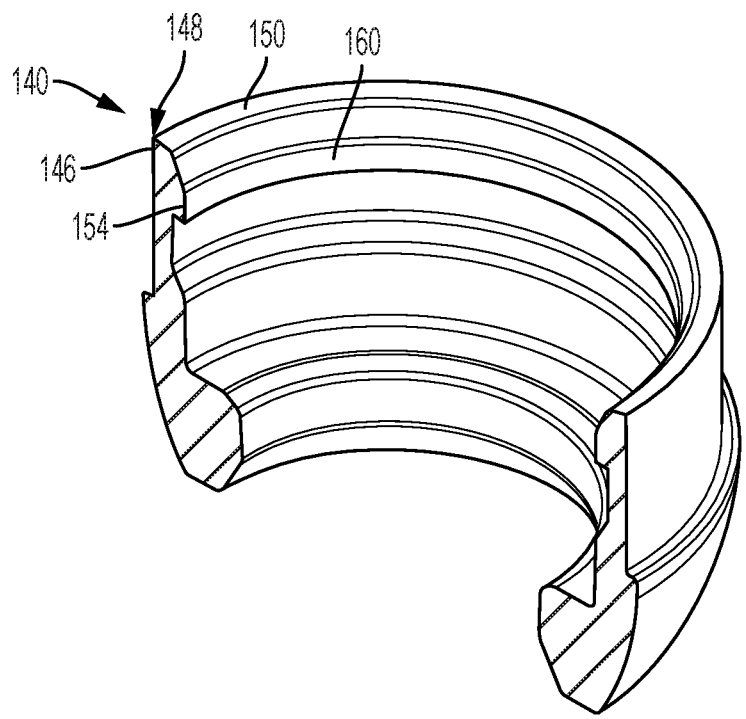
FIG. 5B is a perspective view of a cross section of the second portion of the syringe adapter housing of FIG. 5A.

With specific reference to FIGS. 2B, 3A, 3B, 4A and 4B, the first portion 138 of the housing 112 can further include a plurality of projections 158, such as vertical ridges, configured to engage the second portion 140 to provide the radial interference between the first portion 138 and the second portion 140. For example, as shown in FIGS. 3A and 3B, the projections 158, such as the vertical ridges, can bite or press into the inner surface of the second portion 140 to lock the portions 138, 140 together and, in particular, to prevent or restrict twisting of the first portion 138 relative to the second portion 140. In some examples and as shown in FIGS. 4A and 4B, the projections 158, such as the vertical ridges, can be spaced apart around a circumference of the first portion 138, such as around an outer surface of a recessed vertical cylindrical wall of the first portion 138. The projections 158, such as the vertical ridges, may extend radially outward from the first portion 138 and, for example, can be configured to engage a corresponding inner vertical surface 160 of the second portion 140. In some examples, the projections 158, such as the vertical ridges, can be longitudinally extending ridges spaced equidistantly about the circumference of the first portion 138. In other examples, the projections 158, such as the vertical ridges, can be semi-spherical, cylindrical, pyramid shaped, or any other appropriate shape for contacting the second portion 140 of the housing 112. In other examples, the first portion 138 can be provided with an undulating surface for imparting variable contact with the vertical cylindrical surface 160 of the second portion 140 to lock the first portion 130 to the second portion 132.

Figure 6:
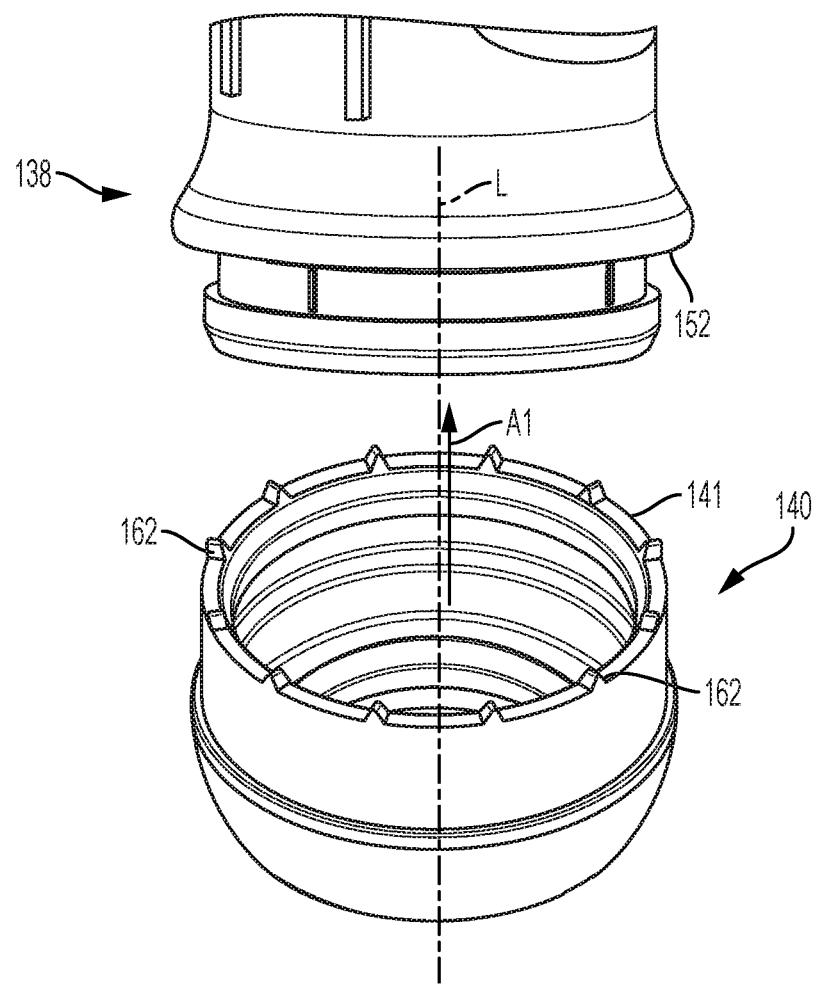
FIG. 6 is an exploded perspective view of the housing of the syringe adapter of FIG. 1.
Figure 7:
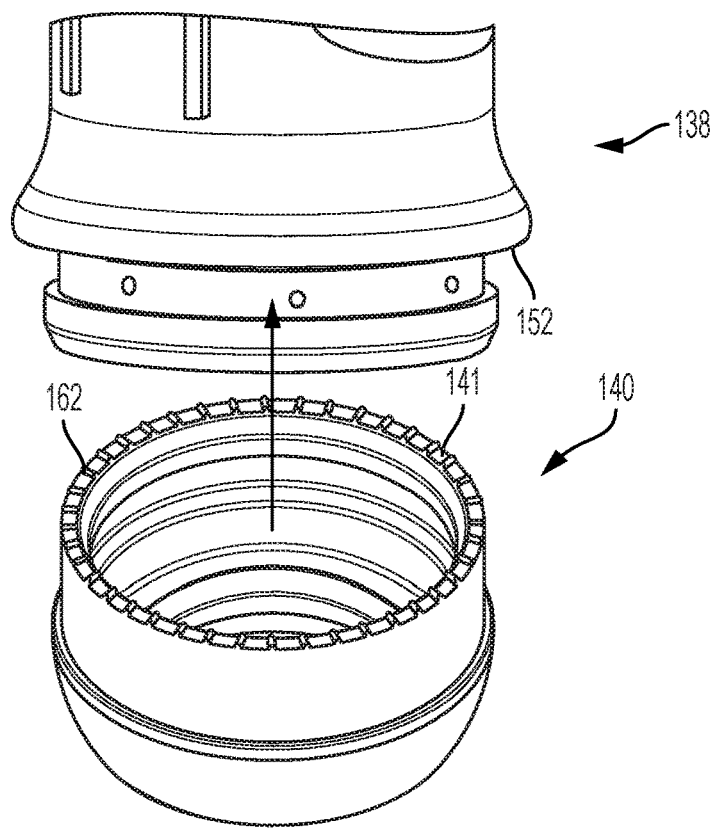
FIG. 7 is an exploded perspective view of another embodiment of a housing of a syringe adapter.
Figure 8:
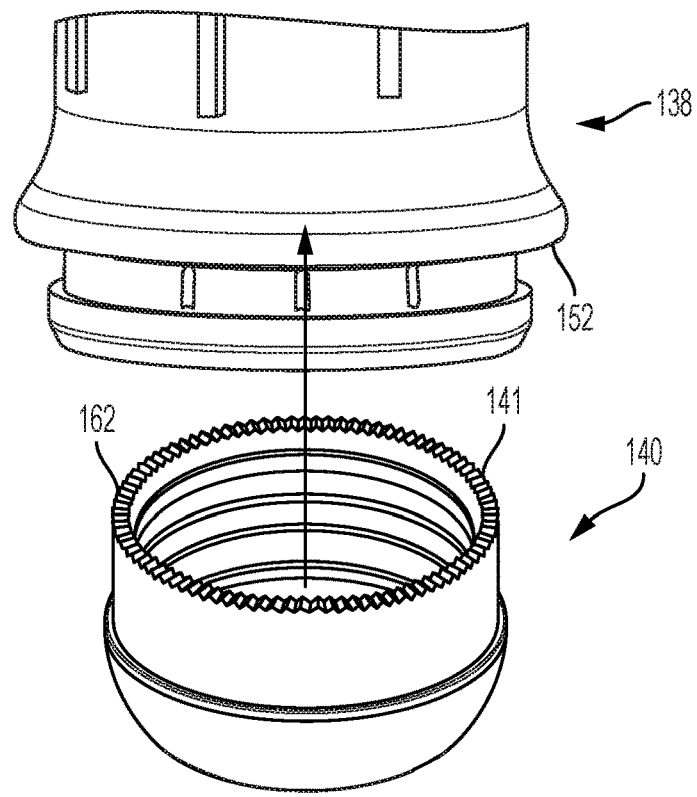
FIG. 8 is an exploded perspective view of another embodiment of a housing of a syringe adapter.
Figure 9A:
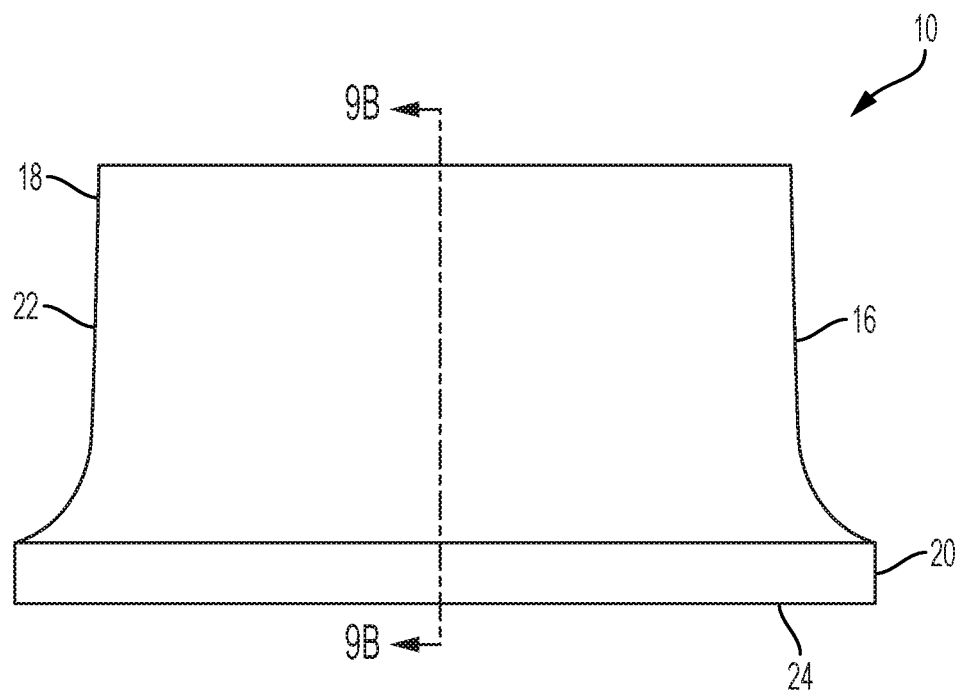
FIG. 9A is a front view of a protective cap for a syringe adapter, according to an aspect of the disclosure.
Figure 9B:
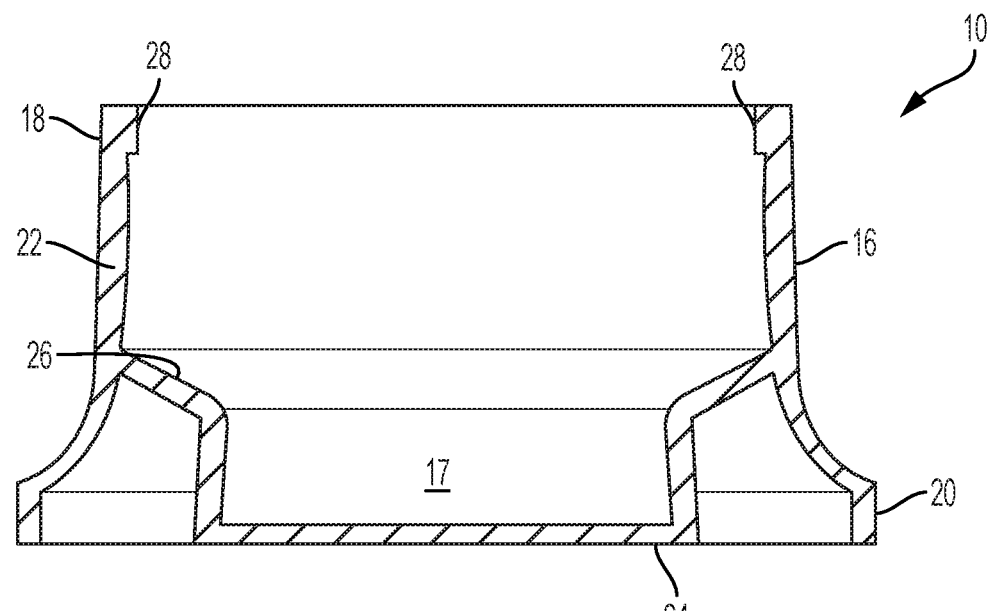
FIG. 9B is a cross-sectional view of the protective cap of FIG. 9A taken along line 9B-9B.
Figure 9C:
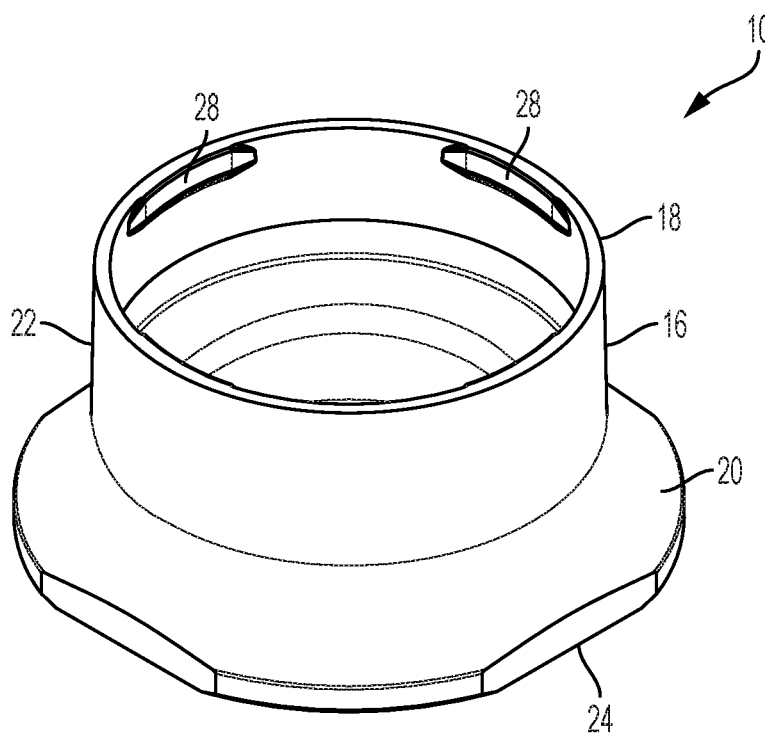
FIG. 9C is a perspective view of the protective cap of FIG. 9A.

With reference to FIGS. 6-8, additional embodiments of the second portion 140 configured to be mounted to the first portion 138 are shown. In the embodiments of FIGS. 6-8, the proximal end 141 of the second portion 140 is shaped to produce uneven distribution of stress between the first portion 138 and the second portion 140 when the second portion 140 is mounted to the first portion 138 in the direction of arrow A1. For example, the second portion 140 can include a plurality of teeth 162 extending axially from the proximal end 141 of the second portion 132. The plurality of teeth 162 are configured to engage the first portion 138 of the adapter housing to provide the axial interference. For example, the plurality of teeth 162 may press into and/or deform the planar interface or surface 152, such as an annular planar wall, of the first portion 138 to form a suitable engagement therebetween. In some examples, as shown in FIGS. 6 and 7, the plurality of teeth 162 can be spaced apart around the annular proximal end 141 of the second portion 140 and, for example, can be separated by a substantially planar surface or by a surface that is sloped radially inwardly toward a longitudinal axis L of the housing. In other examples, as shown in FIG. 8, the plurality of teeth 162 can be connected together around the annular proximal end 141 of the second portion 140. In this configuration, as shown in FIG. 8, the annular proximal end 141 of the second portion does not include any flat or planar regions and, instead, is formed from alternating upwardly sloped and downwardly sloped surfaces around the annular proximal end 141 as shown in FIG. 8.

Exemplary Protective Cap

Examples of a protective cap, which can be mounted to the distal end 118 of the housing 112 and which can be removed from the syringe adapter 110 prior to use, will now be described in detail. With reference to FIGS. 9A-11B, an exemplary cap 10 having the open proximal end 112 and a closed distal end 114 is illustrated. The protective cap 10 is configured to be connected to the adapter housing via a snap fit. For example, the cap 10 can be configured to receive the distal end 118 of the housing 112 within a central cavity 16 as shown, for example, in FIGS. 11A and 11B. The protective cap 10 can be formed from a softer and/or more pliable material than the adapter, such as from soft rubber or pliable plastic. The cap 10 can be formed by injection molding or by another suitable molding process, as is known in the art.

In some examples, the cap 10 includes an annular or main body 16 with a proximal portion 18 configured to engage a syringe adapter, a distal flange or base portion 20, and an annular sidewall 22 extending therebetween. In some examples, the flange or base portion 20 can include a substantially flat bottom surface 24 so that the cap 10 and syringe adapter mounted thereto can be placed on a table or another flat surface in a substantially upright position. In some examples, the annular sidewall 22 of the cap 10 can include a shoulder 26 (shown in FIG. 9B) disposed on a radially inner surface thereof. The shoulder 26 can be an angled surface positioned to contact a portion of the distal end of the syringe adapter to provide additional support for the adapter.

Figure 10:
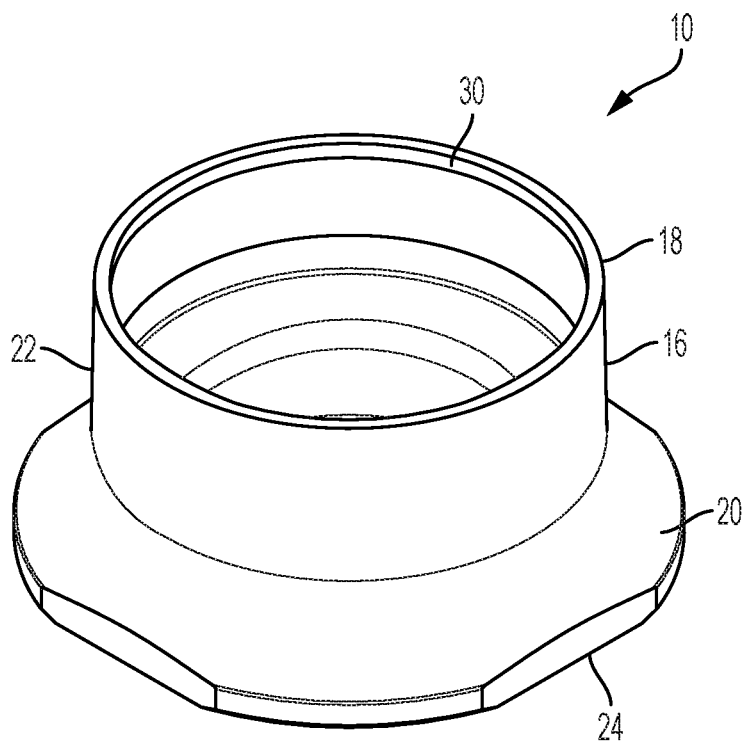
FIG. 10 is a perspective view of another embodiment of a protective cap according to an aspect of the disclosure.
Figure 11A:
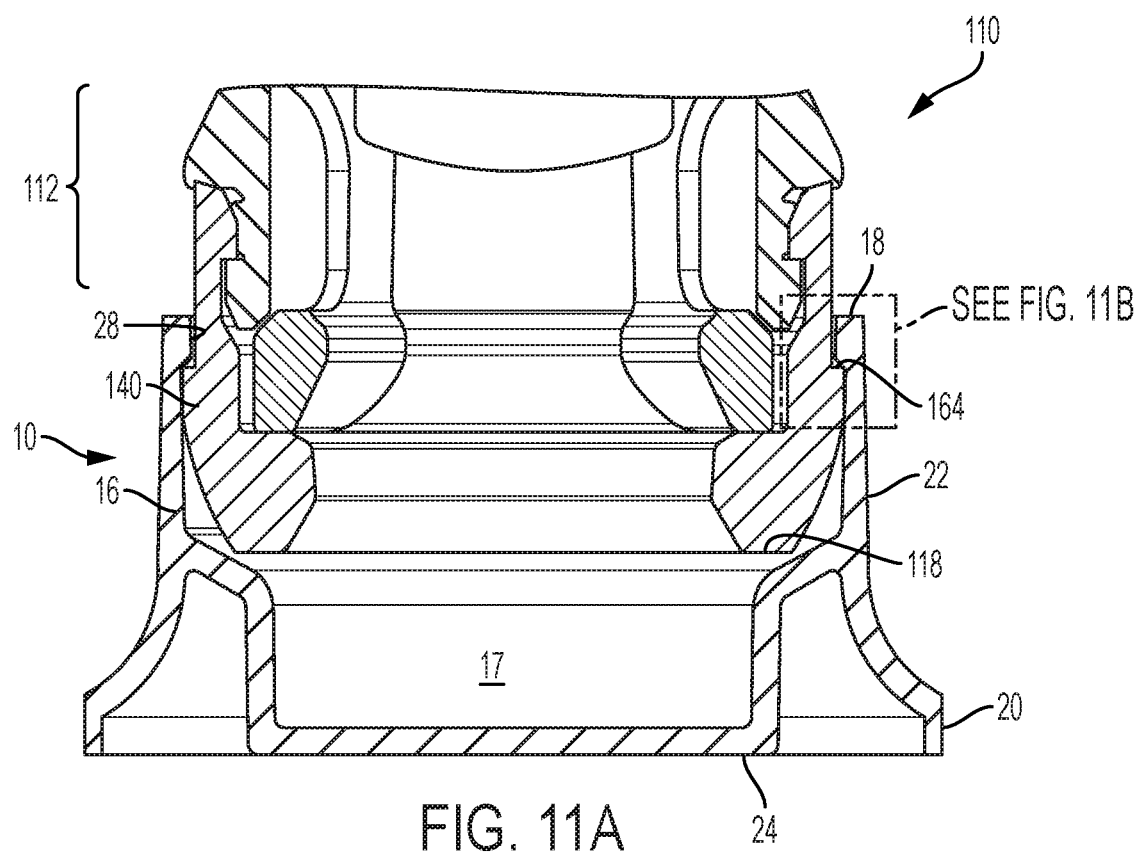
FIG. 11A is a cross-sectional view of a syringe adapter mounted to the protective cap of FIG. 9A.
Figure 11B:
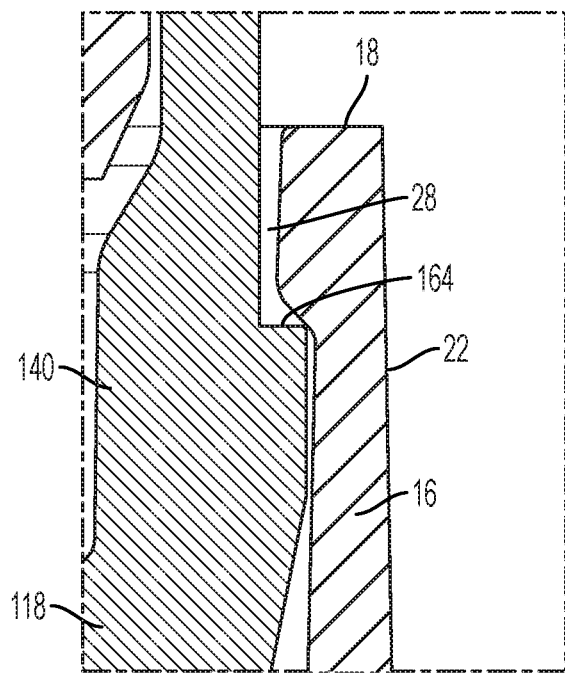
FIG. 11B is an enlarged portion of the cross-sectional view of FIG. 11A enclosed by shape 11B.

Having described the general structure of the cap 10 and syringe adapter 110, structures for mounting the cap 10 to the adapter 110 will now be described in detail. As shown in FIGS. 11A and 11B, in some examples, the proximal portion 18 of the annular body 16 can be configured to form the snap-fit engagement with an open distal end 118 of the syringe adapter 110. For example, the proximal portion 18 of the body 16 may be inwardly biased forming an axial interference engagement between the cap 10 and adapter 110. In some examples, the proximal portion 18 of the annular body 16 may also include one or more protrusions or tabs 28 configured to engage a portion of the distal end 118 of the housing 112 to supplement the snap-fit engagement therebetween. In some examples, the second portion 140 of the adapter housing 112 may include one or more recesses or protrusions positioned to engage the protrusions or tabs 28. For example, the second portion 140 can include an annular groove or shelf 164 extending around the circumference thereof configured to contact the tabs 28 to from a suitable connection therewith. In other examples, the shelf 164 can be replaced with a number of protrusions or detents extending from the outer surface of the second portion 140. The inwardly extending tabs 28 of the cap 10 can be configured to grasp (e.g., form a snap-fit engagement with) the shelf 164 to restrict axial movement of the cap 10 relative to the syringe adapter 110. In some examples, the inwardly directed tabs 28 of the cap annular body 16 can include two or more tabs 28 positioned about the circumference of the proximal portion 18 of the annular body 16. A cap 10 with a proximal portion 18 including four separate individual tabs 28 positioned equidistantly around the circumference of the proximal portion 18 is shown, for example, in FIG. 9C. In other examples, as shown in FIG. 10, the proximal portion 18 of the annular body 16 can include an annular ring or lip 30 extending around the circumference of the proximal portion 18 of the cap annular body 16. The ring or lip 30 can be configured to contact the shelf 164 (shown in FIGS. 11A and 11B) to form a suitable connection therebetween.

Figure 12A:
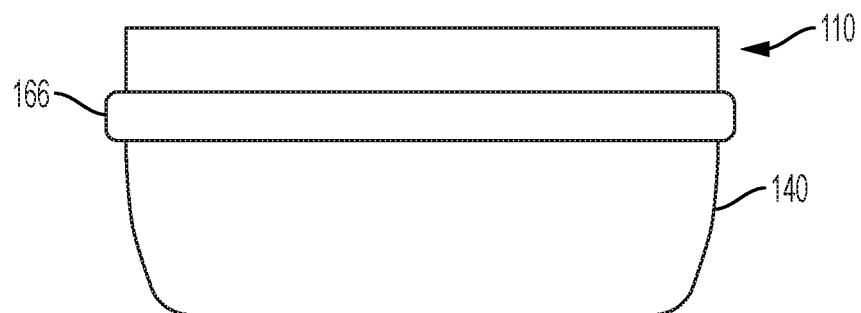
FIGS. 12A-12C are front views of other embodiments of a second portion of a syringe adapter according to aspects of the disclosure.
Figure 12B:
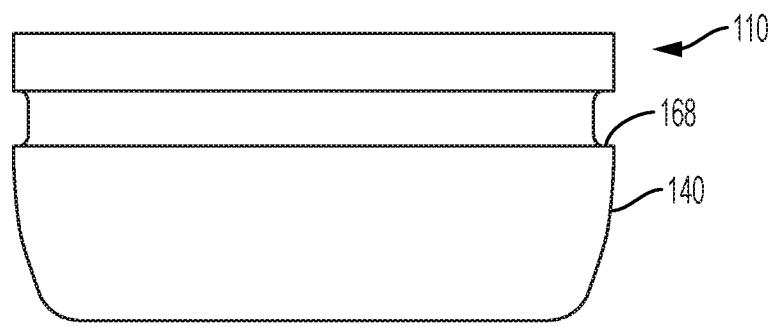
Figure 12C:
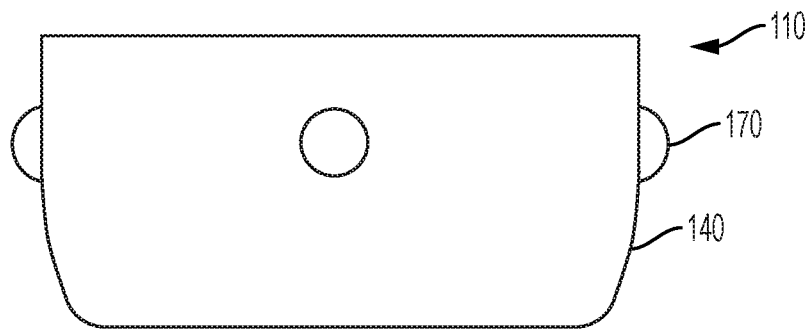

With reference to FIGS. 12A-12C, additional embodiments of a second portion 140 of a syringe adapter 110 are illustrated showing alternative structures for receiving and forming the snap fit with the protective cap 10. For example, as shown in FIG. 12A, the second portion 140 can include a radially outwardly extending band or ridge 166 configured to contact and engage a portion of a protective cap. As shown in FIG. 12B, in other examples, the second portion 140 can include an annular recess or groove 168 configured to receive a tab or annular ring. In still other examples, as shown in FIG. 12C, the second portion 140 of the adapter 110 can include radially outwardly extending protrusions or bumps 170 configured to contact and engage portions of the cap to form the snap-fit therewith. In any case, the cap 10 is designed to be removable from the second portion 140. Accordingly, these interference structures, such as protrusions, grooves, or rings, should be sized to restrict removal of the cap from the syringe adapter 110 to prevent inadvertent exposure of the needle. However, the protrusions, grooves, or rings should be small enough that the cap can be removed by the user without needing to exert unreasonable force or damaging the cap 10 or adapter 110.

Exemplary Protective Caps for Disinfecting the Syringe Adapter

In accordance with another aspect of the disclosure, a protective cap can be configured to permit the user to access the interior of the syringe adapter to disinfect portions of the interior of the syringe adapter prior to use and, in particular, prior to removing the cap from the syringe adapter. An exemplary protective cap 210 which is transitionable between a closed position and an open position to permit access to the interior of a syringe adapter is shown in FIGS. 13A to 15B. With reference to FIGS. 13A-14B, as in previously described examples, the cap 210 includes an open proximal end 212 configured to be connected to an adapter housing via a snap fit. However, unlike in the other examples, the protective cap 210 also includes an open distal end 214 for permitting access to the interior of the syringe adapter. The cap 210 can include an annular or main body 216 with a proximal portion 218 configured to engage a syringe adapter, a distal flange or base portion 220, and an annular sidewall 222 extending therebetween. In some examples, the flange or base portion 220 can include a substantially flat annular bottom surface 224 so that the cap 210 and syringe adapter mounted thereto can be placed on a table or another flat surface in a substantially upright position. In some examples, the annular sidewall 222 of the cap 210 can include a shoulder 226 (shown in FIG. 13B) disposed on a radially inner surface thereof. The shoulder 226 can be an angled surface positioned to contact a portion of the distal end of the syringe adapter to provide additional support for the adapter.

Figure 13A:
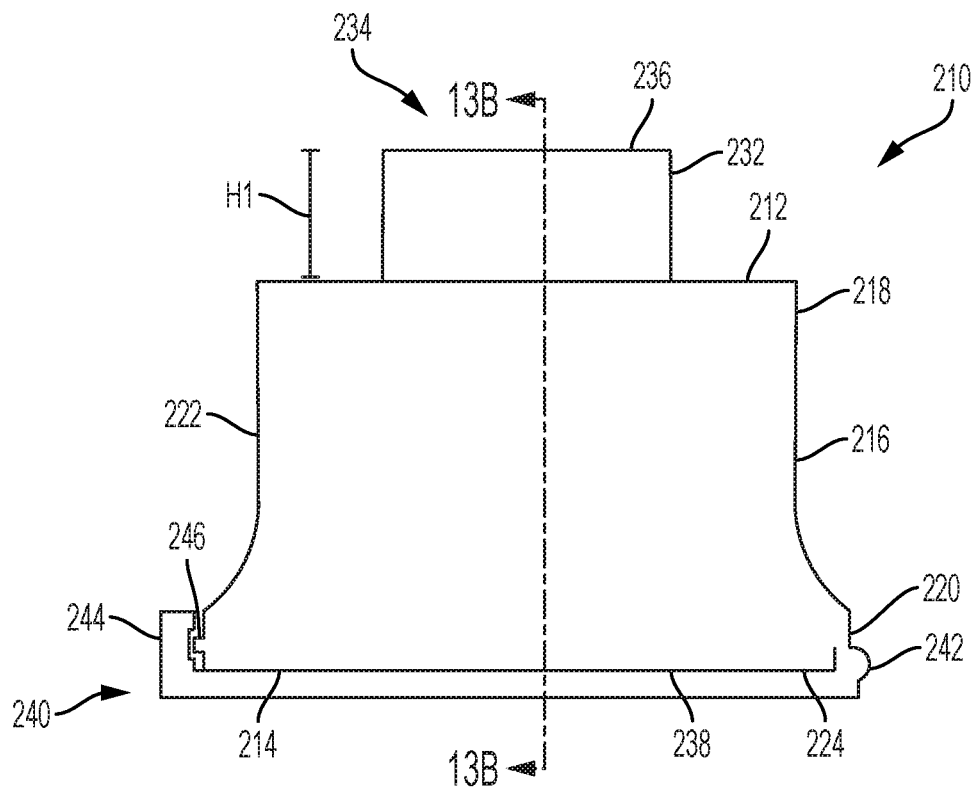
FIG. 13A is a front view of another embodiment of a protective cap for a syringe adapter according to an aspect of the disclosure.
Figure 13B:
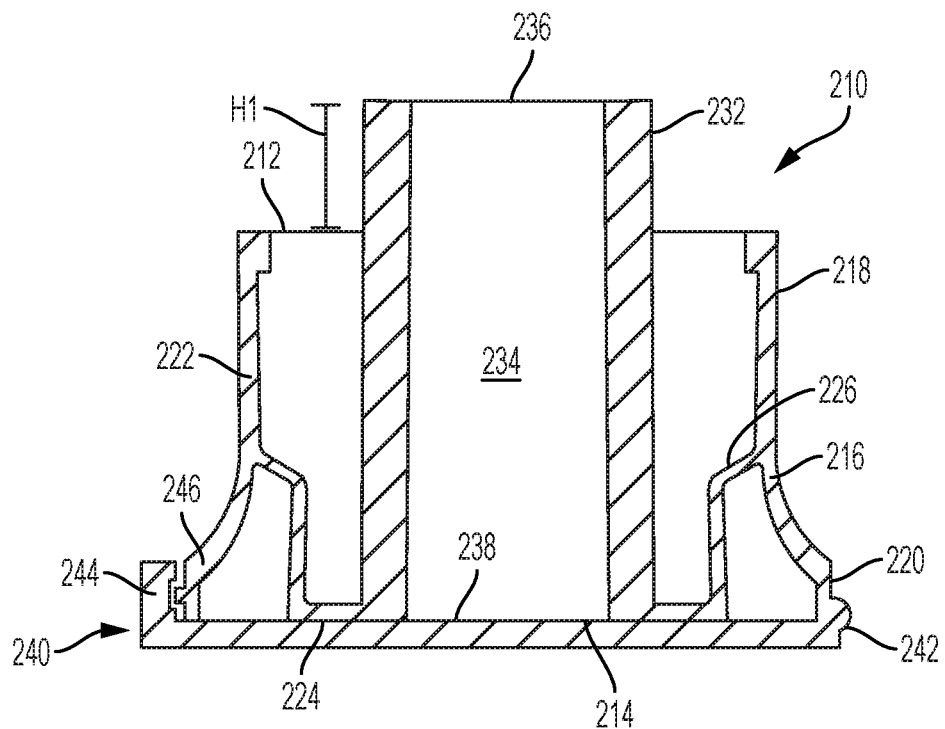
FIG. 13B is cross-sectional view of the protective cap of FIG. 13A taken along line 13B-13B.

The protective cap 210 may further include a retention member, such as a tubular support 232, connected to and extending proximally from the flange or base portion 220 of the main body 216. The tubular support 232 can be configured to be inserted into the open distal end 118 of the syringe adapter 110 (shown in FIGS. 14A and 14B). The tubular support 232 defines a central channel 234 extending between an open proximal end 236 and an open distal end 238 thereof. As shown in FIGS. 13A and 13B, the tubular support 232 may have a circular cross-section configured to be inserted in a corresponding circular open distal end 118 of the syringe adapter 110. In other examples, the tubular support 232 can have different cross-sectional shapes and/or dimensions depending on the size and shape of the open distal end 118 of the syringe adapter 110. The tubular support 232 may extend a distance H1 beyond the proximal portion 218 of the annular body 216 as shown in FIGS. 13A and 13B. In other arrangements, the tubular support 232 may be the same height or may be shorter than the annular body 216 depending on the shape and structure of the syringe adapter 110.

With continued reference to FIGS. 13A to 14B, in some examples, the protective cap 210 also includes a cover 240 connected to the base portion 220 of the annular body 216. The cover 240 may be transitionable from a closed position (shown in FIGS. 13B and 14B) in which it covers the distal open end 238 of the central channel 234 and an open position (shown in FIGS. 15A and 15B) in which the channel 234 is uncovered, thereby allowing a user to access the interior 114 (shown in FIGS. 14A and 14B) of the syringe adapter 110. When the cap 210 is in the open position (shown in FIGS. 15A and 15B), a user can insert a swab through the open distal end 238 of the central channel 234 and open distal end 118 of the syringe adapter 110 for disinfecting the interior 114 of the syringe adapter 110. The cover 240 can be connected and/or mounted to the base portion 220 of the annular body 216 by any type of connector or fastener suitable for forming a pivotal engagement or joint between the cover 240 and base portion 220. In one example, the cover 240 is integrally formed with the base portion 220 of the annular body 216 and connected together by a living hinge 242. A living hinge 242 can be a thin flexible region (e.g., a bend line) between two more rigid portions of a structure. A living hinge 242 can be formed by thinning or cutting into rigid pieces to form a bend line at a desired position between the two rigid pieces. Alternatively, a cap 210 including the thinned out living hinge 242 can be formed during molding.

With continued reference to FIGS. 13A to 14B, in some examples, the cover 240 and/or base portion 220 of the annular body 216 can include a locking or latching mechanism for maintaining the cover 240 in the closed position. For example, the cover 240 can include a proximally extending lip including a detent 244 configured to engage a corresponding portion of the annular body 216. For example, the detent 244 can be positioned to engage a corresponding projection or protrusion 246 on the base portion 220 of the annular body 216 to form an interference engagement therewith.

Figure 14A:
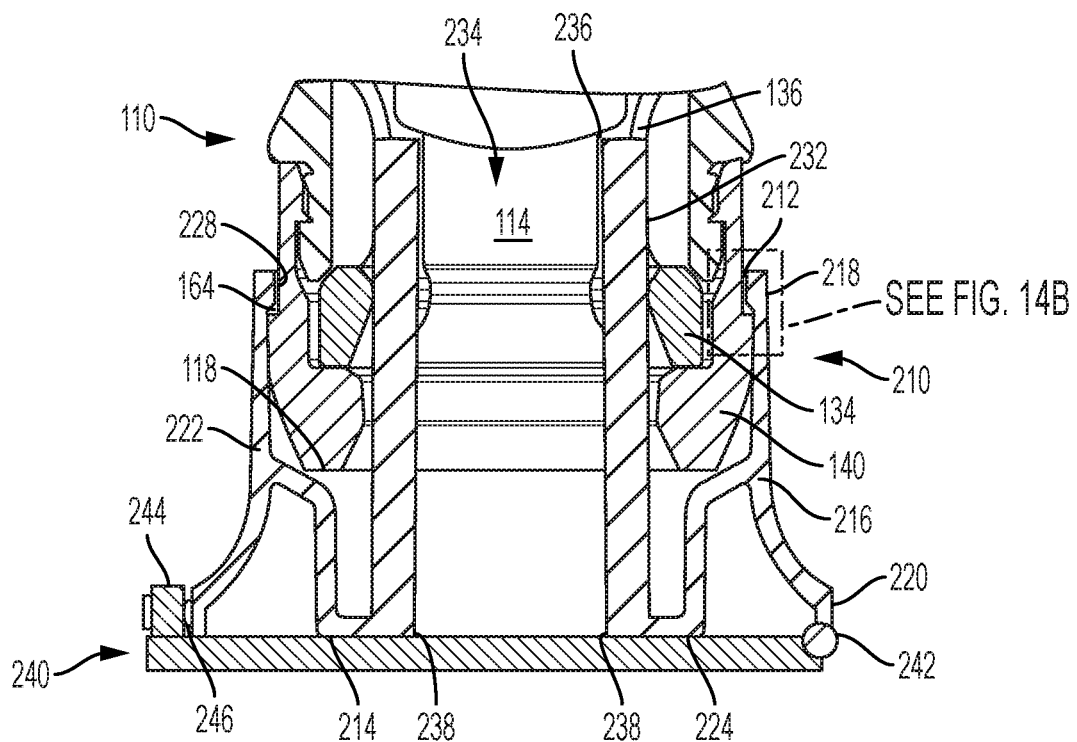
FIG. 14A is a cross-sectional view of a syringe adapter mounted to the protective cap of FIG. 13A.
Figure 14B:
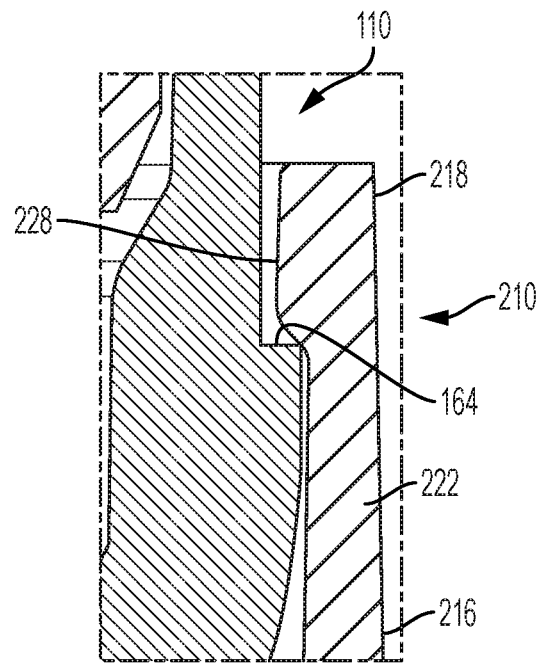
FIG. 14B is a cross-sectional view of the portion of the adapter and cap of FIG. 14A enclosed by shape 14B.

With specific reference to FIGS. 14A and 14B, as in previously described examples, the proximal portion 218 of the annular body 216 can be configured to form the snap-fit engagement with the open distal end 118 of the syringe adapter 110. For example, the proximal portion 218 of the cap 210 may be inwardly biased forming an axial interference engagement between the cap 210 and the syringe adapter 110. In some examples, the proximal portion 218 of the annular body 216 may include one or more protrusions or tabs 228 configured to engage a portion of the distal end 118 of the housing 112 to form the removable snap-fit engagement therebetween. For example, as in previously described examples, the second portion 140 of the adapter housing 112 may include an annular groove or shelf 164 extending around the circumference thereof.

As shown in FIG. 14A, when the cap 210 is mounted to the syringe adapter 110, the tubular support 232 is inserted into the interior 114 of the adapter 110, such that the proximal open end 236 of the central channel 234 extends up to or beyond the collet flange 134 and/or collet legs 136. In this position, the outer surface of the tubular support 32 can contact the flange 134 and/or legs 136 pressing the flange 134 and/or legs 136 radially outwardly towards their recessed positions. Therefore, the tubular support 232 can hold the flange 134 and/or legs 136 away from the central channel 234 of the tubular support 232 and the open distal end 118 of the syringe adapter 110, such that they are not displaced when a swab is inserted into the adapter 110.

Figure 15A:
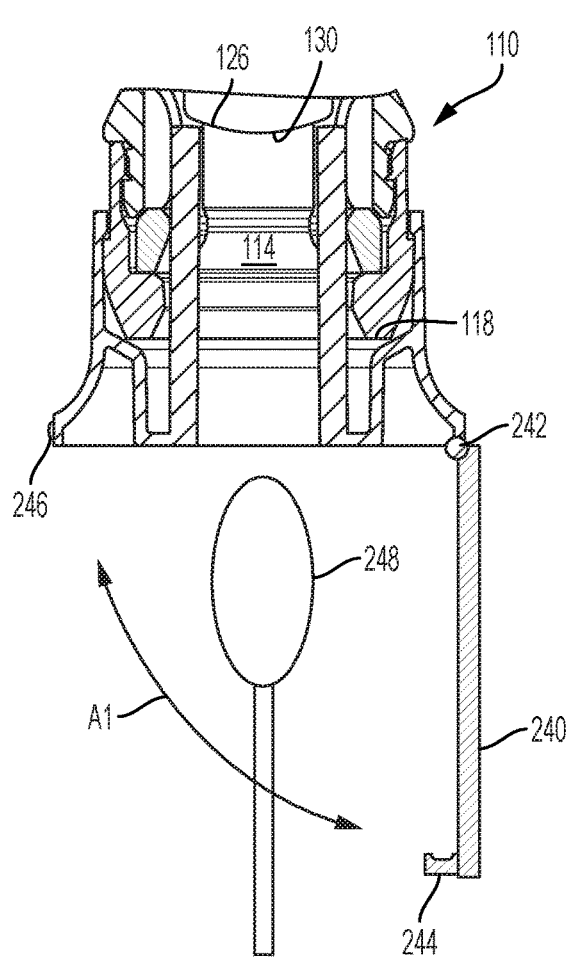
FIG. 15A is a schematic drawing of a swab prior to insertion into the protective cap of FIG. 13A according to an aspect of the disclosure.
Figure 15B:
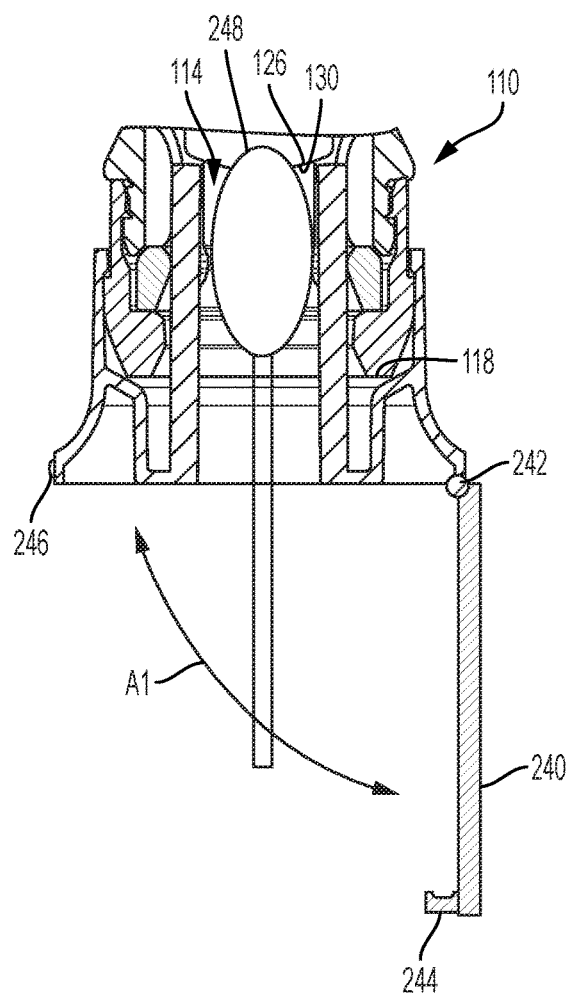
FIG. 15B is a schematic drawing showing the swab of FIG. 15A inserted into the open cap.

With reference to FIGS. 15A and 15B, steps for disinfecting the interior 114 of the syringe adapter 110 will be described. As shown in FIG. 15A, a user, such as a clinician, can open the cover 240 by pulling a portion of the cover 240 away from the annular body 216 with sufficient force to overcome the latching mechanism engagement between the detent 244 and protrusion 246. Once the interference engagement between the detent 244 and protrusion 246 is overcome, the cover 240 swings in a downward direction as shown by arrow A1 to its open position. As discussed herein, the cover 240 can be connected to the annular body 216 by a flexible and/or pivoting joint, such as a living hinge 242. Accordingly, the cover 240 rotates or pivots about the joint or living hinge 242 from the closed position to the open position. Once the cover 240 is in its open position, the user advances a swab 248 containing a disinfecting agent toward the open distal end 118 of the adapter 110 in the direction of arrow A2 as shown in FIG. 15A. As shown in FIG. 15B, once the swab 248 is inserted into the interior 114 of the adapter 110, the user may move the swab in a radial fashion thereby contacting elements of the adapter interior and, in particular, elements of the sealing arrangement 126. For example, the user may disinfect a distal surface of the membrane or septum 130 to ensure that the cannula 124 (shown in FIG. 3A) is not contaminated when it pierces the septum 130. Once disinfecting is complete, the user can remove the swab 248 from the interior 114 of the syringe adapter 110 and close the cover 240 by swinging it back to its closed position in the direction of arrow A1 to prevent contamination of the interior 114 and/or septum 130. The closed position is illustrated, for example, in FIGS. 13B and 14A.

Exemplary Protective Cap Configured to be Inserted in the Open Distal End of the Syringe Adapter With reference to FIGS. 16A and 16B, another exemplary embodiment of an assembly for connecting a syringe to a patient connector including the syringe adapter 110 and a cap 310 is illustrated. The adapter 110 is substantially similar to previously described adapters and includes the housing 112 having a proximal end 116 configured to be mounted directly or indirectly to the syringe and an open distal end 118 configured to be removably mounted to the protective cap 310. The cap 310 includes an annular body 316 having a proximal portion 318 extending from a flange or base portion 320. Unlike in previously described examples in which the open distal end 118 of the adapter 110 is inserted into the annular body of the cap, for the cap 310, the proximal portion 318 of the body 316 can be sized and shaped to be inserted into the distal open end 118 of the syringe adapter 110 to mount the syringe adapter 110 to the cap 310. For example, the proximal portion 318 of the annular body 316 may be slightly larger (e.g., have a slightly larger diameter) than the distal open end 118 of the syringe adapter 110, such that when inserted into the open distal end 118 of the adapter 110, a frictional engagement between the cap 310 and adapter 110 is formed. As in previously described examples, the cap 310 can be formed from a soft flexible and/or elastomeric material such that it deforms slightly when inserted into the adapter 110. The resiliency of the cap 310 can contribute to the frictional engagement between the adapter 110 and the cap 310. The proximal portion 318 of the annular body 316 can also include a flange or lip 350 (shown in FIG. 16B) configured to contact the open distal end 118 of the adapter 110 to restrict or prevent a user from pulling the cap 310 from the adapter 110. As in previously described examples, the cap 310 can also include a cover 340 connected to the base portion 320 of the annular body 316. The cover 340 can be transitionable from a closed position in which it covers a distal open end 338 of the annular body 316, and an open position in which a swab is capable of being inserted through the open end 338 and open distal end 118 of the syringe adapter 110 for disinfecting the interior 114 of the syringe adapter 110.

Exemplary Protective Cap with Swab or Pad

Figure 17A:
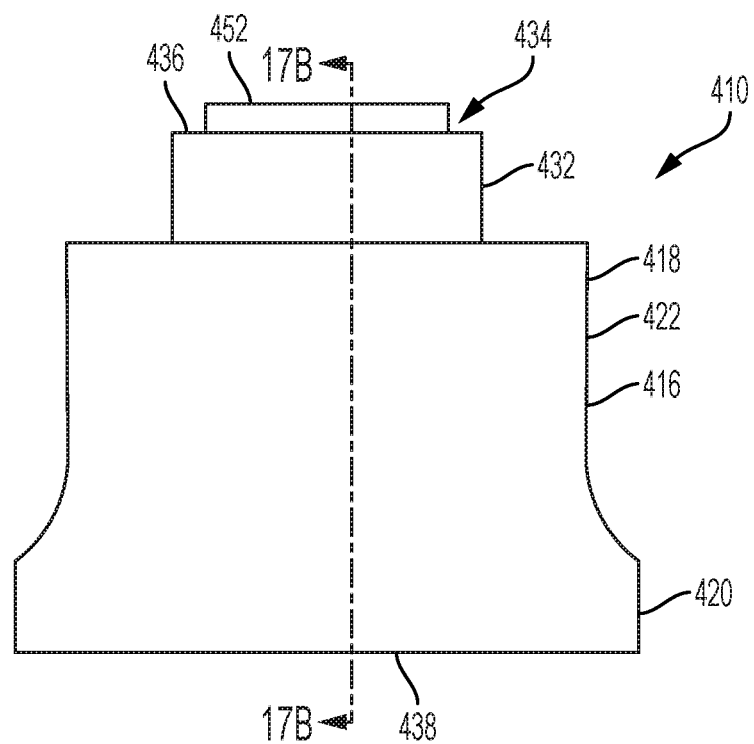
FIG. 17A is a front view of another embodiment of a protective cap for a syringe adapter according to an aspect of the disclosure.
Figure 17B:
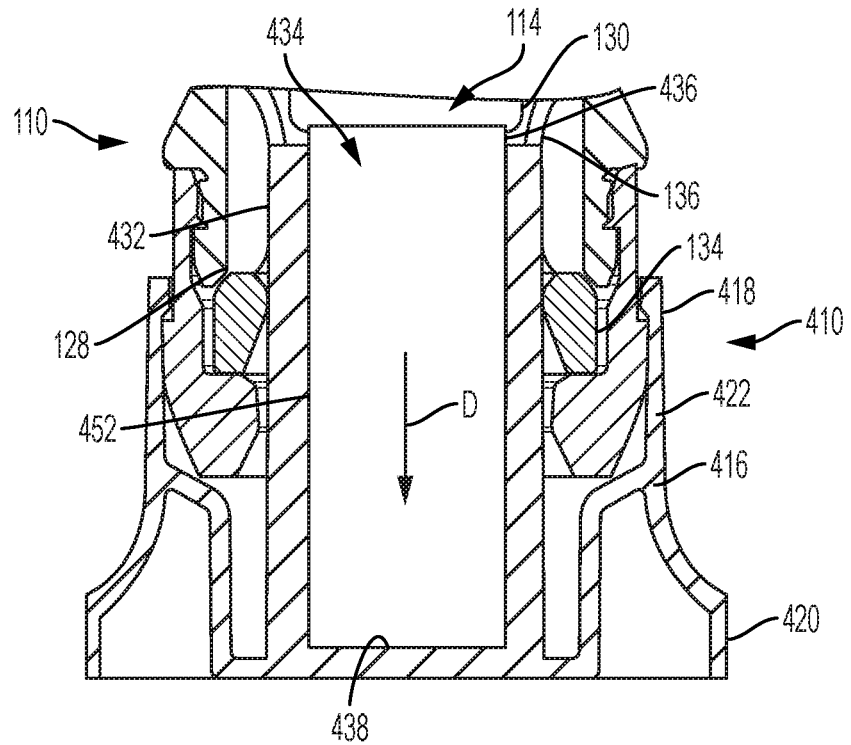
FIG. 17B is a cross-sectional view of the protective cap of FIG. 17A taken along line 17B-17B and connected to a syringe adapter.

With reference to FIGS. 17A and 17B, another exemplary embodiment of a cap 410 for a syringe adapter 110 (shown in FIG. 17B) is illustrated. As in previously described examples, the cap 410 includes an annular body 416 having a proximal portion 418 configured to engage the syringe adapter 110, a distal base portion 420, and an annular sidewall 422 extending therebetween. As in previously described examples, the cap 410 also includes a retention member, such as a tubular support 432, connected to and extending proximally from the base portion 420 of the annular body 416. The tubular support 432 can include or define a central channel 434 extending between an open proximal end 436 and a closed distal end 438 thereof. Unlike in previously described examples, in which the cap is configured to permit a user to insert a swab into the interior of the adapter 110, the cap 410 includes a swab or pad 452 mounted within the central channel 434 of the tubular support 432. The swab or pad 452 can be formed from an absorbent material, such as cotton or other types of absorbent fibers. The swab or pad 452 can be wetted with a disinfecting solution, such as isopropyl alcohol, for disinfecting the interior 114 of the adapter 110. For example, the swab or pad 452 can be used to disinfect a distal surface of the membrane or septum 130 (shown in FIG. 17B). As shown in FIG. 17B, when the cap 410 is mounted to the syringe adapter 110, the outer surface of the tubular support 432 contacts the collet flange 134 and collet legs 136 to maintain the flange 134 and legs 136 in their recessed positions. The swab or pad 452 protrudes beyond the open proximal end 436 of the central cavity 434 of the tubular support 432 into the interior 114 of the adapter 110. For example, a proximal end of the swab or pad 452 can come into face-to-face contact with the membrane or septum 130 to disinfect the septum 130. Disinfecting the septum 130 prior to activation of the adapter 110 can prevent or reduce contamination of the needle cannula 124 (shown in FIG. 2A), which pierces the septum 130. When ready to connect the adapter 110 to the patient connector, the user removes the cap 410, such as by pulling the cap 410 in a distal direction D with sufficient force to overcome an axial interference engagement between the cap 410 and distal end 118 of the adapter 110, thereby exposing the open distal end 118 of the adapter 110. Once the cap 410 is removed, the user can insert a portion of the patient connector through the open distal end 118 of the adapter 110. The flange 134 and/or legs 136 of the collet 128 grasp the inserted portion of the patient connector to form a suitable engagement therebetween. The adapter 110 can then be activated in the manner described herein, by moving the collet 128 in a proximal direction, thereby causing the cannula 124 to pierce the septum 130 and engage the patient connector (not shown).

Although the invention has been described in detail for the purpose of illustration based on what is currently considered to be the most practical and preferred aspects, it is to be understood that such detail is solely for that purpose and that the invention is not limited to the disclosed aspects, but, on the contrary, is intended to cover modifications and equivalent arrangements that are within the spirit and scope of the appended claims. For example, it is to be understood that the present invention contemplates that, to the extent possible, one or more features of any aspect can be combined with one or more features of any other aspect.

The invention claimed is:

1. A syringe adapter comprising:
   a housing having a first end and a second end positioned opposite the first end, the housing comprising
   a first portion enclosing an interior of the housing comprising an annular planar wall, a recessed vertical cylindrical wall, and a plurality of vertical ridges extending radially outward from an outer surface of the recessed vertical cylindrical wall, and
   a second portion comprising a wall enclosing the interior of the housing connected to the first portion, the first end of the housing comprising a connector configured to be secured to a syringe barrel;
   a cannula positioned within the housing;
   a seal arrangement positioned within the housing and movable through the first and second portions of the housing, the seal arrangement comprising a membrane; and
   a protective cap connected to the second portion of the housing via a snap fit, the protective cap comprising an open first end, a second end, an annular sidewall extending between the first end and the second end, and an annular shoulder extending radially inward from the annular sidewall and proximally from the second end of the protective cap, the annular shoulder having an end intersecting the annular sidewall distal from the first open end of the protective cap and another end intersecting the second end of the protective cap,
   wherein the annular planar wall of the first portion of the housing directly contacts an annular top surface of the wall of the second portion providing an axial interference, which restricts pulling the first portion away from the second portion of the housing and pushing the first portion farther into the second portion of the housing, and
   wherein the recessed vertical cylindrical wall and plurality of vertical ridges extending from the recessed vertical cylindrical wall of the first portion of the housing directly contact an inner surface of the wall of the second portion providing a radial interference, which restricts twisting of the first portion of the housing relative to the second portion of the housing.

2. The syringe adapter of claim 1, wherein the annular top surface of the wall of the second portion of the housing comprises an annular triangular interface, and wherein the annular triangular interface of the second portion of the housing engages the annular planar wall of the first portion of the housing to provide the axial interference that restricts pushing the first portion of the housing farther into the second portion of the housing.

3. The syringe adapter of claim 2, wherein the annular planar wall of the first portion of the housing comprises an annular horizontal wall that extends about perpendicularly to a longitudinal axis of the housing and faces towards the second end of the housing.

4. The syringe adapter of claim 3, wherein the annular triangular interface of the second portion of the housing comprises a pointed end configured to engage a portion of the annular horizontal wall of the first portion of the housing.

5. The syringe adapter of claim 4, wherein the annular triangular interface of the second portion of the housing further comprises a radially inwardly sloped surface extending from the pointed end of the annular triangular interface.

6. The syringe adapter of claim 1, wherein the plurality of vertical ridges are spaced apart around a circumference of the recessed vertical cylindrical wall of the first portion of the housing.

7. The syringe adapter of claim 1, wherein the plurality of vertical ridges are configured to press into the inner surface of the wall of the second portion of the housing, when the first portion of the housing is connected to the second portion of the housing.

8. A syringe adapter comprising:
   a housing having a first end and a second end positioned opposite the first end, the housing comprising
   a first portion enclosing an interior of the housing comprising an annular planar wall, a recessed vertical cylindrical wall, and a plurality of vertical ridges extending radially outward from an outer surface of the recessed vertical cylindrical wall, and a second portion comprising a wall enclosing the interior of the housing connected to the first portion, the first end of the housing comprising a connector configured to be secured to a syringe barrel;

a cannula positioned within the housing; and a seal arrangement positioned within the housing and movable through the first and second portions of the housing, the seal arrangement comprising a membrane, wherein the annular planar wall of the first portion of the housing directly contacts an annular top surface of the wall of the second portion providing an axial interference, which restricts pulling the first portion away from the second portion of the housing and pushing the first portion farther into the second portion of the housing, and wherein the recessed vertical cylindrical wall and plurality of vertical ridges extending from the recessed vertical cylindrical wall of the first portion of the housing directly contact an inner surface of the wall of the second portion providing a radial interference, which restricts twisting of the first portion of the housing relative to the second portion of the housing, wherein the second portion of the housing comprises a plurality of teeth extending axially from the annular top surface of the wall of the second portion towards the first end of the housing, the plurality of teeth of the second portion of the housing engaging the annular wall of the first portion of the housing to provide the axial interference, which restricts pushing the first portion of the housing farther into the second portion of the housing.

9. The syringe adapter of claim 8, wherein each of the plurality of teeth are configured to press into the annular planar wall of the first portion of the housing, when the second portion of the housing is connected to the first portion of the housing.

10. The syringe adapter of claim 8, wherein the plurality of teeth provide uneven distribution of stress between the annular planar wall of the first portion of the housing and the annular top surface of the second portion of the housing, when the second portion of the housing is connected to the first portion of the housing.

11. The syringe adapter of claim 8, wherein the plurality of teeth are spaced apart and separated by the annular top surface of the second portion of the housing.

12. The syringe adapter of claim 1, wherein the connector is rotatably mounted to the first portion of the housing, and wherein the cannula is secured to the connector and at least partially enclosed within the housing.

13. The syringe adapter of claim 1, wherein the annular shoulder of the protective cap contacts the second end of the housing when the second end of the housing is inserted into the protective cap.

14. The syringe adapter of claim 13, wherein the second end of the protective cap comprises a base portion comprising a flange extending radially outward from the annular sidewall of the protective cap and a bottom surface, the flange and the bottom surface being separated by an annular recess at least partially closed by the annular shoulder.

15. The syringe adapter of claim 1, wherein the wall of the second portion of the housing comprises an annular groove, and wherein the protective cap comprises one or more tabs extending radially inward from the annular sidewall of the protective cap that engage the annular groove of the second portion of the housing, thereby securing the protective cap to the second portion of the housing.

16. The syringe adapter of claim 1, wherein the second end of the protective cap comprises a removable cover that moves between an open position and a closed position.

17. The syringe adapter of claim 16, wherein the protective cap comprises a tubular support that extends into the second end of the housing and engages a portion of the seal arrangement to prevent movement of the seal arrangement and the membrane with respect to the cannula, and wherein the tubular support defines a central channel, which provides access to the interior of the housing via the second end of the protective cap when the removable cover is in the open position.

18. The syringe adapter of claim 16, wherein, when the removable cover is in the open position, a swab can be inserted through the central channel of the protective cap and second end of the housing for disinfecting at least a portion of the seal arrangement.

\* \* \* \* \*